US009023363B2

(12) United States Patent
Czerkinsky et al.

(10) Patent No.: US 9,023,363 B2

(45) Date of Patent: May 5, 2015

(54) A1 MOIETY OF CHOLERA TOXIN A SUBUNIT AS AN ADJUVANT FOR MUCOSAL AND SYSTEMIC VACCINES

(75) Inventors: Cecil Czerkinsky, Seoul (KR); Manki Song, Seoul (KR)

(73) Assignee: International Vaccine Institute, Seoul (KR)

( * ) Notice: Subject to any disclaimer, the term of this patent is extended or adjusted under 35 U.S.C. 154(b) by 227 days.

(21) Appl. No.: 12/603,211

(22) Filed: Oct. 21, 2009

(65) Prior Publication Data

US 2014/0227312 A1 Aug. 14, 2014

Related U.S. Application Data

(60) Provisional application No. 61/107,179, filed on Oct. 21, 2008.

(51) Int. Cl.

| | |
|---|---|
| ***A61K 39/385*** | (2006.01) |
| ***A61K 39/02*** | (2006.01) |
| ***A61K 39/00*** | (2006.01) |
| ***A61K 39/108*** | (2006.01) |
| ***C07K 1/00*** | (2006.01) |
| ***C07K 14/00*** | (2006.01) |
| ***C07K 17/00*** | (2006.01) |
| ***C12N 9/10*** | (2006.01) |
| ***A61K 39/21*** | (2006.01) |
| ***A61K 39/39*** | (2006.01) |

(52) U.S. Cl.

CPC .............. *C12N 9/1051* (2013.01); *A61K 39/21* (2013.01); *A61K 39/39* (2013.01); *A61K 2039/541* (2013.01); *A61K 2039/55544* (2013.01); *C07K 2319/10* (2013.01); *C07K 2319/55* (2013.01)

(58) Field of Classification Search

None

See application file for complete search history.

(56) References Cited

PUBLICATIONS

Agren et al.: "Genetically engineered nontoxic vaccine adjuvant that combines B cell targeting with immunomodulation by cholera toxin A1 subunit", The Journal of Immunology, vol. 158, No. 8, Apr. 15, 1997, pp. 3936-3946.

Aagren et al.: :Hydrophobicity engineering of cholera toxin A1 subunit in the strong adjuvant fusion protein CTA1-DD, Protein Engineering, vol. 12, No. 2, Feb. 1, 1999, pp. 173-178.

Aagren et al.: Adjuvanticity of the Cholera Toxin A1-Based Gene Fusion Protein, CTA1-DD, is Critically Dependent on the ADP-Ribosyltransferase and IG-Binding Activity, The Journal of Immunology, vol. 162, No. 4, Jan. 1, 1999, pp. 2432-2440.

Anonymous: "Molecular Vaccinology", International Vaccine Institute, 2013.

Bowen et al.: "Cholera Toxin Acts as a Potent Adjuvant for the Induction of Cytotoxic T-Lymphocyte Responses with Non-Replicating Antigens", Immunology, vol. 81, No. 3, Mar. 1, 1994, pp. 338-342.

Kabouridis: "Biological Applications of Protein Transduction Technology", Trends in Biotechnology, vol. 21, No. 11, Nov. 1, 2003, pp. 498-503.

Ryu et al.: "Enhanced uptake of a heterologous protein with an HIV-1 Tat protein transduction domains (PTD) at both termini", Molecules and Cells, vol. 16, No. 3, Dec. 1, 2003, pp. 385-391.

European Extended Search Report dated Apr. 26, 2013 for European Application No. 09821667.4, 7 pages.

*Primary Examiner* — Gary Nickol

*Assistant Examiner* — Lakia Tongue

(74) *Attorney, Agent, or Firm* — Knobbe, Martens, Olson & Bear LLP

(57) ABSTRACT

The present invention relates to cholera toxin CTA1 protein fragments, adjuvant compositions, and methods relating to adjuvants for vaccines. The invention also relates to using recombinant CTA1 fragments conjugated to a polypeptide containing a protein transduction domain or cell-penetrating peptide as an immunomodulator.

20 Claims, 17 Drawing Sheets

Fig.1.Schematic representation of PTD CTA1 fusion protein (TCTA1T) expression vectors (left) and purification of the TCTA1T protein from E. coli (right).

| groups | IgG | IgG1 | IgG2a |
|---|---|---|---|
| PBS | 8.33 ± 2.07 | 11.81 ± 1.17 | 5.69 ± 0.11 |
| TCTA1T | 17.67 ± 0.82 | 19.26 ± 0.41 | 8.93 ± 0.50 |
| TmCTA1T | 14.00 ± 0.89 | 15.47 ± 0.56 | 6.33 ± 0.95 |
| CT | 18.00 ± 0.63 | 19.69 ± 0.28 | 10.96 ± 1.19 |

Fig. 2. OVA-specific serum IgG responses of mice immunized nasally with TCTA1T, TmCTA1T or CT as an adjuvant. Groups of 5 mice were immunized nasally on days 0, 14, 28 with 20 ug of OVA alone, with 10 ug of TCTA1T, TmCTA1T or 2 ug of CT. Serum sample were collected on days 13, 27, 41.

| groups | Saliva IgA | Nasal wash IgA | Lung wash IgA | Lung tissue IgA |
|---|---|---|---|---|
| PBS | N.D | 1.33 ± 0.82 | N.D | 1.17 ± 0.41 |
| TCTA1T | 8.50 ± 0.55 | 8.67 ± 0.82 | 12.83 ± 0.98 | 11.33 ± 0.52 |
| TmCTA1T | N.D | 3.50 ± 2.07 | 5.17 ± 2.99 | 5.83 ± 2.64 |
| CT | 9.83 ± 0.75 | 8.50 ± 0.55 | 9.80 ± 0.45 | 10.00 ± 0.89 |

Fig. 3. OVA-specific mucosal antibody responses of mice immunized nasally with TCTA1T, TmCTA1T or CT as an adjuvant. Saliva were collected on days 13, 27, 41. Lung tissue, Lung wash, and nasal wash sample were collected on days 14 after third immunization.

Fig. 4. OVA-specific Ab producing cells in spleen and lung of mice immunized nasally with TCTA1T, TmCTA1T or CT. Ab producing cells were measured on days 7 after third immunization.

Fig. 5. OVA-specific mucosal and systemic antibody responses of mice immunized nasally with various doses of TCTA1T as an adjuvant. Saliva and Serum were collected on days 13, 27, 41.

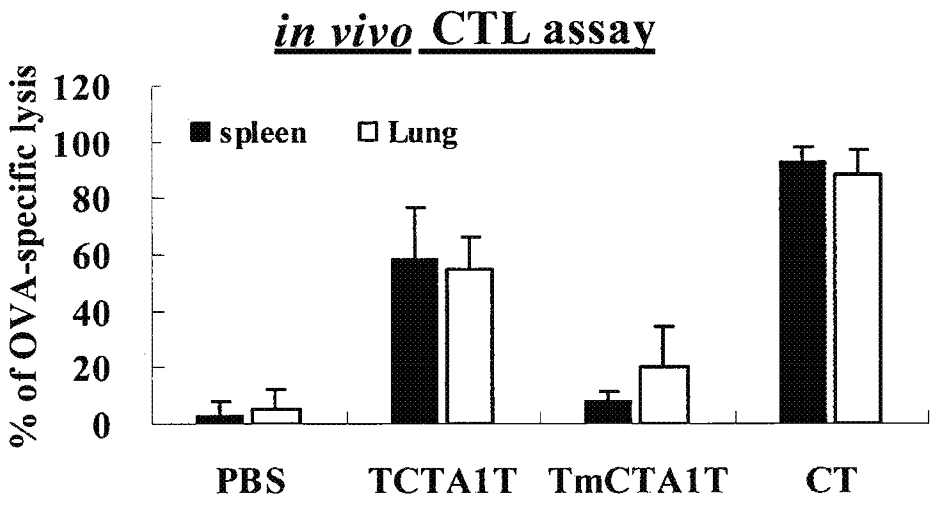
Fig. 6. OVA-specific $CD8^+$ cytotoxic T cell response in spleen and lung of mice immunized nasally with TCTA1T, TmCTA1T or CT.

Fig. 7. Weight loss and survival in mice challenge by intranasal inoculation with 10 $LD_{50}$ of A/PR/8 . 2 weeks after the second immunization.

| Groups | Intestinal loop (mg/cm) | cAMP (pmol/ml) | Footpad Edema (mm) |
|---|---|---|---|
| PBS | 36.90 ± 1.24 | 2.53 ± 0.08 | 2.40 ± 0.10 |
| TCTA1T | 42.40 ± 1.65 | 6.71 ± 0.90 | 2.6 ± 0.20 |
| TmCTA1T | 35.00 ± 3.35 | 2.48 ± 0.38 | 2.50 ± 0.10 |
| CT | 156.30 ± 33.11 | 43.56 ± 11.21 | 4.80 ± 0.60 |

Fig. 8. *In vitro* and *In vivo* Toxicity of TCTA1, TmCTA1 or CT through cAMP test, footpad edema, intestinal loop test.

Fig.9.Schematic representation of CTA1 expression vectors (left) and purification of the CTA1 protein from E. coli (right).

Fig. 10 A
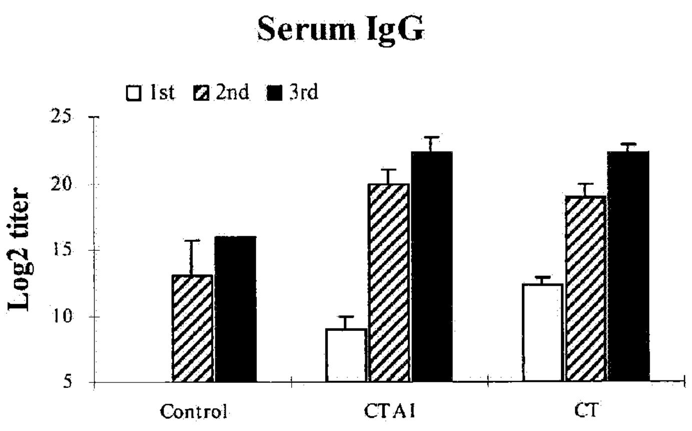
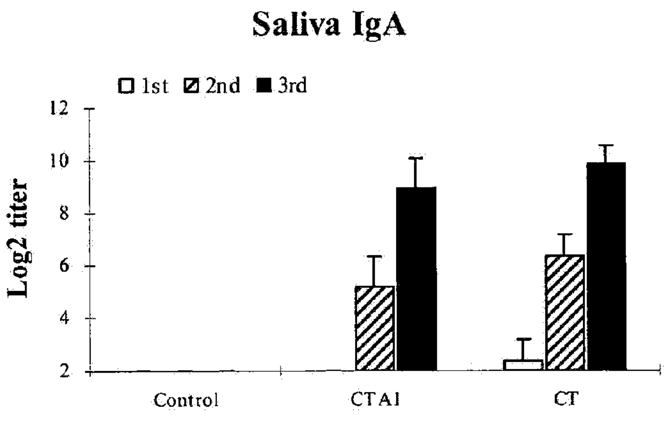
Fig. 10 B
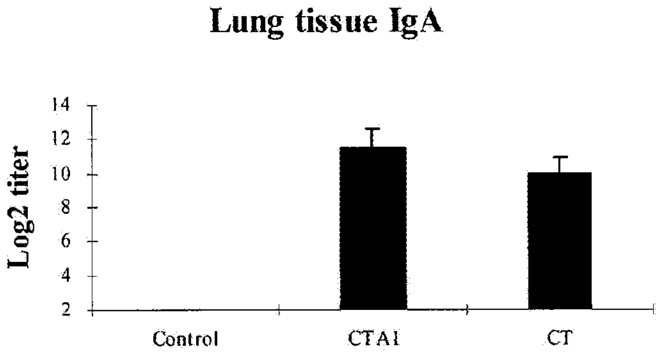
Fig. 10 C
Fig. 10. OVA-specific antibody responses of mice immunized nasally with CTA1 as an adjuvant. Serum and saliva were collected on days 13, 27, 41. Lung tissue was collected on days 14 after third immunization.

Fig. 11. OVA-specific Ab producing cells in spleen and lung of mice immunized nasally with CTA1 plus OVA. Ab producing cells were measured on days 7 after third immunization.

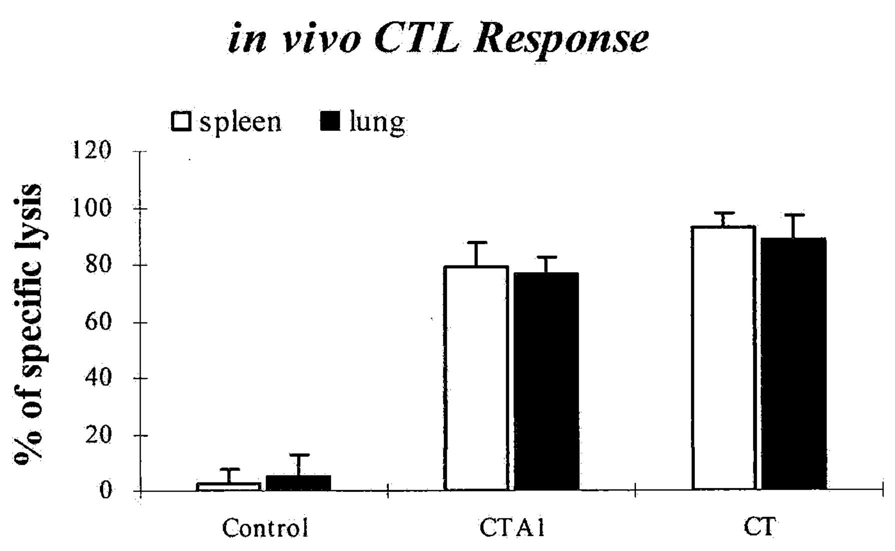
Fig. 12. OVA-specific $CD8^+$ cytotoxic T cell response in spleen and lung of mice immunized nasally with CTA1 plus OVA.

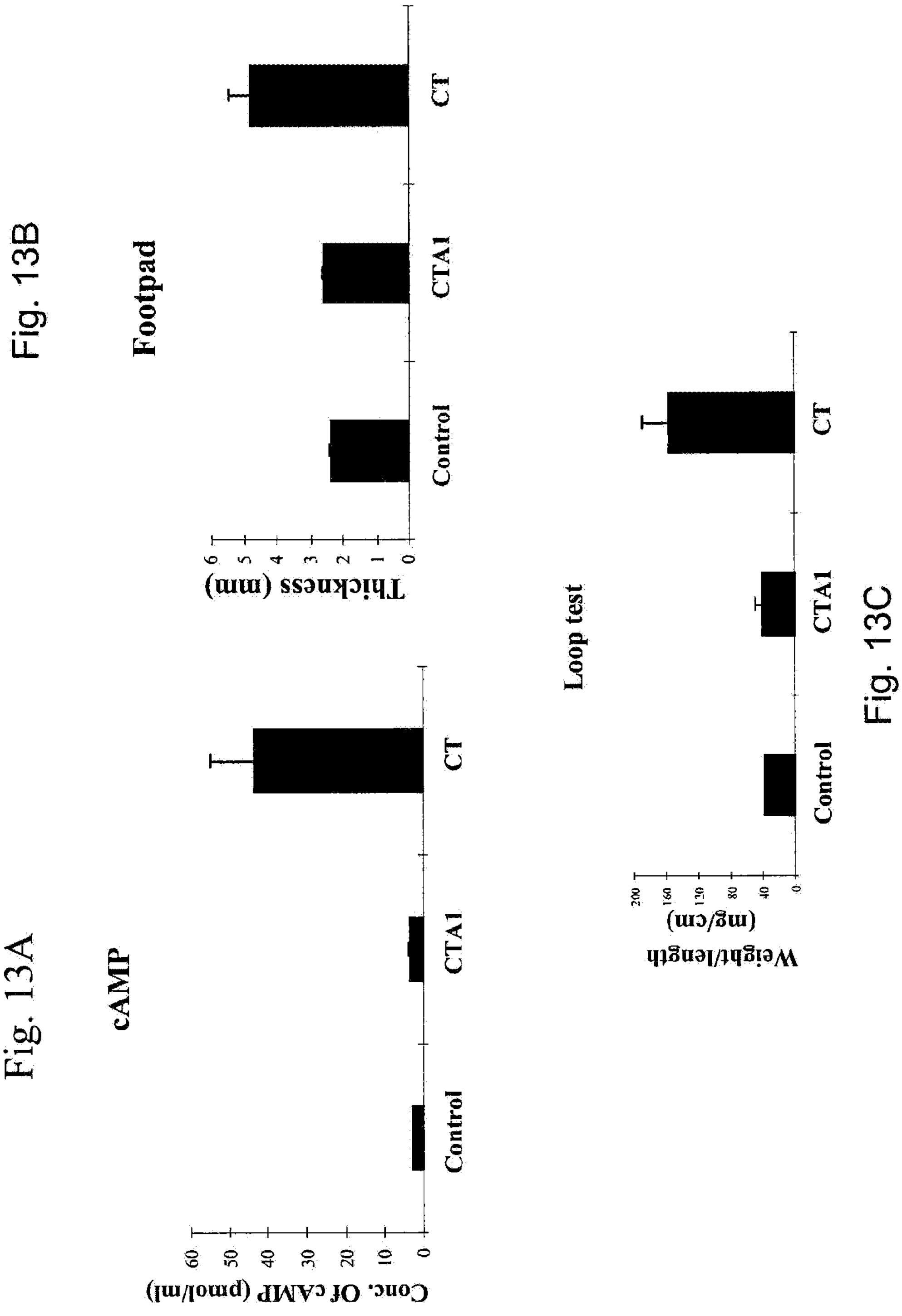
Fig. 13. *In vitro* and *In vivo* Toxicity of CTA1 through cAMP test, footpad edema, intestinal loop test.

Cholera toxin A DNA sequence from NCBI (SEQ ID NO:1)

*ATGGTAAAGATAATATTTGTGTTTTTTATTTTCTTATCATCATTTTCATATGCA*AATGATGATAAGTTATATCGGGCAGAT
TCTAGACCTCCTGATGAAATAAAGCAGTCAGGTGGTCTTATGCCAAGAGGACAGAGTGAGTACTTTGACCGAGGTACTCAA
ATGAATATCAACCTTTATGATCATGCAAGAGGAACTCAGACGGGATTTGTTAGGCACGATGATGGATATGTTTCCACCTCA
ATTAGTTTGAGAAGTGCCCACTTAGTGGGTCAAACTATATTGTCTGGTCATTCTACTTATTATATATATGTTATAGCCACT
GCACCCAACATGTTTAACGTTAATGATGTATTAGGGGCATACAGTCCTCATCCAGATGAACAAGAAGTTTCTGCTTTAGGT
GGGATTCCATACTCCCAAATATATGGATGGTATCGAGTTCATTTTGGGGTGCTTGATGAACAATTACATCGTAATAGGGGC
TACAGAGATAGATATTACAGTAACTTAGATATTGCTCCAGCAGCAGATGGTTATGGATTGGCAGGTTTCCCTCCGGAGCAT
AGAGCTTGGAGGGAAGAGCCGTGGATTCATCATGCACCGCCGGGTTGTGGGAATGCTCCAAGATCATCGATCAGTAATACT
TGCCATCAAAAAACCCAAAGTCTAGGTGTAAAATTCCTTGACGAATACCAATCTAAAGTTAAAAGACAAATATTTTCAGGC
TATCAATCTGATATTGATACACATAATAGAATTAAGGATGAATTATGA italicized: deleted sequence; shaded sequence: CTA1; underlined sequence: CT-A2

Fig. 14B pET15b-CTA1 (SEQ ID NO:2)

*ATGGGCAGCAGCCATCATCATCATCA*TCACAGCAGCGGCCTGGTGCCGCGCGGCAGCCATATGAATGATGATAAGTTATAT
CGGGCAGATTCTAGACCTCCTGATGAAATAAAGCAGTCAGGTGGTCTTATGCCAAGAGGACAGAGTGAGTACTTTGACCGA
GGTACTCAAATGAATATCAACCTTTATGATCATGCAAGAGGAACTCAGACGGGATTTGTTAGGCACGATGATGGATATGTT
TCCACCTCAATTAGTTTGAGAAGTGCCCACTTAGTGGGTCAAACTATATTGTCTGGTCATTCTACTTATTATATATATGTT
ATAGCCACTGCACCCAACATGTTTAACGTTAATGATGTATTAGGGGCATACAGTCCTCATCCAGATGAACAAGAAGTTTCT
GCTTTAGGTGGGATTCCATACTCCCAAATATATGGATGGTATCGAGTTCATTTTGGGGTGCTTGATGAACAATTACATCGT
AATAGGGGCTACAGAGATAGATATTACAGTAACTTAGATATTGCTCCAGCAGCAGATGGTTATGGATTGGCAGGTTTCCCT
CCGGAGCATAGAGCTTGGAGGGAAGAGCCGTGGATTCATCATGCACCGCCGGGTTGTGGGA*ATGCTCCAAGATCATCGTAG*
GGATCC

Fig. 14C pET15b-TCTA1T (SEQ ID NO:3)

ATGGGCAGCAGCCATCATCATCATCATCACAGCAGCGGCCTGGTGCCGCGCGGCAGCCATAGGAAGAAGCGGAGAC
AGCGACGAAGACTCGAGAATGATGATAAGTTATATCGGGCAGATTCTAGACCTCCTGATGAAATAAAGCAGTCAGGTG
GTCTTATGCCAAGAGGACAGAGTGAGTACTTTGACCGAGGTACTCAAATGAATATCAACCTTTATGATCATGCAAGAGGAA
CTCAGACGGGATTTGTTAGGCACGATGATGGATATGTTTCCACCTCAATTAGTTTGAGAAGTGCCCACTTAGTGGGTCAAA
CTATATTGTCTGGTCATTCTACTTATTATATATATGTTATAGCCACTGCACCCAACATGTTTAACGTTAATGATGTATTAG
GGGCATACAGTCCTCATCCAGATGAACAAGAAGTTTCTGCTTTAGGTGGGATTCCATACTCCCAAATATATGGATGGTATC
GAGTTCATTTTGGGGTGCTTGATGAACAATTACATCGTAATAGGGGCTACAGAGATAGATATTACAGTAACTTAGATATTG
CTCCAGCAGCAGATGGTTATGGATTGGCAGGTTTCCCTCCGGAGCATAGAGCTTGGAGGGAAGAGCCGTGGATTCATCATG
CACCGCCGGGTTGTGGGAATGCTCCAAGATCATCGGGATCCAGGAAGAAGCGGAGACAGCGACGAAGATAGGTC
GAG

Bold: PTD

Fig. 14D pET15b-TmCTXA1T (SEQ ID NO:4)

ATGGGCAGCAGCCATCATCATCATCATCACAGCAGCGGCCTGGTGCCGCGCGGCAGCCATAGGAAGAAGCGGAGAC
AGCGACGAAGACTCGAGAATGATGATAAGTTATATCGGGCAGATTCTAGACCTCCTGATGAAATAAAGCAGTCAGGTG
GTCTTATGCCAAGAGGACAGAGTGAGTACTTTGACCGAGGTACTCAAATGAATATCAACCTTTATGATCATGCAAGAGGAA
CTCAGACGGGATTTGTTAGGCACGATGATGGATATGTTTCCACCAAGATTAGTTTGAGAAGTGCCCACTTAGTGGGTCAAA
CTATATTGTCTGGTCATTCTACTTATTATATATATGTTATAGCCACTGCACCCAACATGTTTAACGTTAATGATGTATTAG
GGGCATACAGTCCTCATCCAGATGAACAAGAAGTTTCTGCTTTAGGTGGGATTCCATACTCCCAAATATATGGATGGTATC
GAGTTCATTTTGGGGTGCTTGATGAACAATTACATCGTAATAGGGGCTACAGAGATAGATATTACAGTAACTTAGATATTG
CTCCAGCAGCAGATGGTTATGGATTGGCAGGTTTCCCTCCGGAGCATAGAGCTTGGAGGGAAGAGCCGTGGATTCATCATG
CACCGCCGGGTTGTGGGAATGCTCCAAGATCATCGGGATCCAGGAAGAAGCGGAGACAGCGACGAAGATAGGTC
GAG

Bold: PTD mCTA1 sequence ; Ser-63 → Lys, TCA (S) → AAG (K)

TCTA1T (PTD-CTA1-PTD) amino acid sequence; Underlined sequences are PTD motif   (complete fragment is SEQ ID NO:5)

<u>RKKRRQRRR</u>LENDDKLYRADSRPPDEIKQSGGLMPRGQSEYFDRGTQMNINLYDHA
RGTQTGFVRHDDGYVSTSISLRSAHLVGQTILSGHSTYYIYVIATAPNMFNVNDVLGA
YSPHPDEQEVSALGGIPYSQIYGWYRVHFGVLDEQLHRNRGYRDRYYSNLDIAPAA
DGYGLAGFPPEHRAWREEPWIHHAPPGCGNAPRSSGS<u>RKKRRQRRR</u>

Fig. 15B

Bold underlined sequence is CTA1 amino acid fragment; complete sequence is from GI:169247721 (Genbank ID) (SEQ ID NO:6)

MVKIIFVFFIFLSSFSYA**<u>NDDKLYRADSRPPDEIKQSGGLMPRGQSEYFDRGTQMNINLYDHA
RGTQTGFVRHDDGYVSTSISLRSAHLVGQTILSGHSTYYIYVIATAPNMFNVNDVLGAYSPHP
DEQEVSALGGIPYSQIYGWYRVHFGVLDEQLHRNRGYRDRYYSNLDIAPAADGYGLAGFPPEH
RAWREEPWIHHAPPGCGNAPRSS</u>**MSNTCDEKTQSLGVKFLDEYQSKVKRQIFSGYQSDIDTHN
RIKDEL

Fig. 15C

HIV tat amino acid sequence GI:2801502(Genbank ID), including the underlined PTD motif. (complete fragment is SEQ ID NO:7)

MEPVDPRLEPWKHPGSQPKTACTNCYCKKCCFHCQVCFITKALGISYG<u>RK
KRRQRRR</u>AHQNSQTHQASLSKQPTSQPRGDPTGPKE

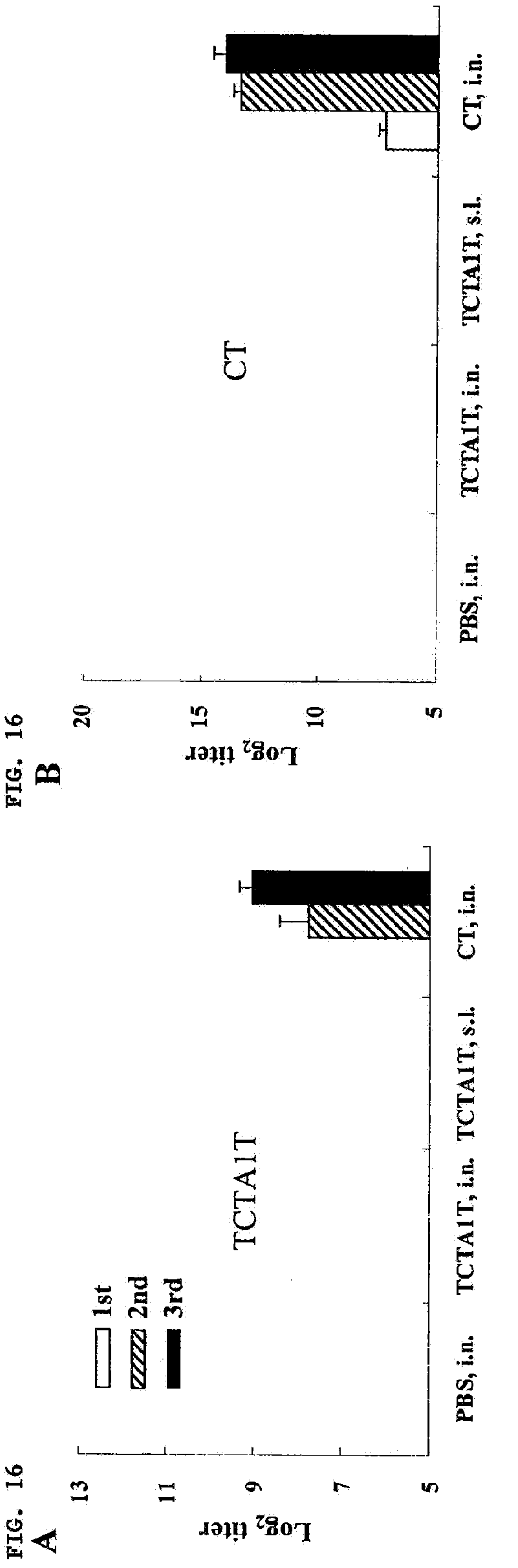
Fig. 16. Reactogenic responses in mice administered with TCTA1T or CT as an adjuvant.

SEQUENCE LISTING

<160> NUMBER OF SEQ ID NOS: 16

<210> SEQ ID NO 1
<211> LENGTH: 777
<212> TYPE: DNA
<213> ORGANISM: Vibrio cholera

<400> SEQUENCE: 1
atggtaaaga taatatttgt gtttttttatt ttcttatcat cattttcata tgcaaatgat 60
gataagttat atcgggcaga ttctagacct cctgatgaaa taaagcagtc aggtggtctt 120
atgccaagag gacagagtga gtactttgac cgaggtactc aaatgaatat caacctttat 180
gatcatgcaa gaggaactca gacgggattt gttaggcacg atgatggata tgtttccacc 240
tcaattagtt tgagaagtgc ccacttagtg ggtcaaacta tattgtctgg tcattctact 300
tattatatat atgttatagc cactgcaccc aacatgttta acgttaatga tgtattaggg 360
gcatacagtc ctcatccaga tgaacaagaa gtttctgctt taggtgggat tccatactcc 420
caaatatatg gatggtatcg agttcatttt ggggtgcttg atgaacaatt acatcgtaat 480
aggggctaca gagatagata ttacagtaac ttagatattg ctccagcagc agatggttat 540
ggattggcag gtttccctcc ggagcataga gcttggaggg aagagccgtg gattcatcat 600
gcaccgccgg gttgtgggaa tgctccaaga tcatcgatca gtaatacttg cgatgaaaaa 660
acccaaagtc taggtgtaaa attccttgac gaataccaat ctaaagttaa aagacaaata 720
ttttcaggct atcaatctga tattgataca cataatagaa ttaaggatga attatga 777

<210> SEQ ID NO 2
<211> LENGTH: 654
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2
atgggcagca gccatcatca tcatcatcac agcagcggcc tggtgccgcg cggcagccat 60
atgaatgatg ataagttata tcgggcagat tctagacctc ctgatgaaat aaagcagtca 120

| | |
|---|---|
| ggtggtctta tgccaagagg acagagtgag tactttgacc gaggtactca aatgaatatc | 180 |
| aacctttatg atcatgcaag aggaactcag acgggatttg ttaggcacga tgatggatat | 240 |
| gtttccacct caattagttt gagaagtgcc cacttagtgg gtcaaactat attgtctggt | 300 |
| cattctactt attatatata tgttatagcc actgcaccca acatgtttaa cgttaatgat | 360 |
| gtattagggg catacagtcc tcatccagat gaacaagaag tttctgcttt aggtgggatt | 420 |
| ccatactccc aaatatatgg atggtatcga gttcattttg gggtgcttga tgaacaatta | 480 |
| catcgtaata ggggctacag agatagatat tacagtaact tagatattgc tccagcagca | 540 |
| gatggttatg gattggcagg tttccctccg gagcatagag cttggaggga agagccgtgg | 600 |
| attcatcatg caccgccggg ttgtgggaat gctccaagat catcgtaggg atcc | 654 |

<210> SEQ ID NO 3
<211> LENGTH: 717
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

| | |
|---|---|
| atgggcagca gccatcatca tcatcatcac agcagcggcc tggtgccgcg cggcagccat | 60 |
| aggaagaagc ggagacagcg acgaagactc gagaatgatg ataagttata tcgggcagat | 120 |
| tctagacctc ctgatgaaat aaagcagtca ggtggtctta tgccaagagg acagagtgag | 180 |
| tactttgacc gaggtactca aatgaatatc aacctttatg atcatgcaag aggaactcag | 240 |
| acgggatttg ttaggcacga tgatggatat gtttccacct caattagttt gagaagtgcc | 300 |
| cacttagtgg gtcaaactat attgtctggt cattctactt attatatata tgttatagcc | 360 |
| actgcaccca acatgtttaa cgttaatgat gtattagggg catacagtcc tcatccagat | 420 |
| gaacaagaag tttctgcttt aggtgggatt ccatactccc aaatatatgg atggtatcga | 480 |
| gttcattttg gggtgcttga tgaacaatta catcgtaata ggggctacag agatagatat | 540 |
| tacagtaact tagatattgc tccagcagca gatggttatg gattggcagg tttccctccg | 600 |
| gagcatagag cttggaggga agagccgtgg attcatcatg caccgccggg ttgtgggaat | 660 |
| gctccaagat catcgggatc caggaagaag cggagacagc gacgaagata ggtcgag | 717 |

<210> SEQ ID NO 4
<211> LENGTH: 717
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

| | |
|---|---|
| atgggcagca gccatcatca tcatcatcac agcagcggcc tggtgccgcg cggcagccat | 60 |
| aggaagaagc ggagacagcg acgaagactc gagaatgatg ataagttata tcgggcagat | 120 |
| tctagacctc ctgatgaaat aaagcagtca ggtggtctta tgccaagagg acagagtgag | 180 |
| tactttgacc gaggtactca aatgaatatc aacctttatg atcatgcaag aggaactcag | 240 |
| acgggatttg ttaggcacga tgatggatat gtttccacca agattagttt gagaagtgcc | 300 |
| cacttagtgg gtcaaactat attgtctggt cattctactt attatatata tgttatagcc | 360 |
| actgcaccca acatgtttaa cgttaatgat gtattagggg catacagtcc tcatccagat | 420 |

-continued

```
gaacaagaag tttctgcttt aggtgggatt ccatactccc aaatatatgg atggtatcga    480

gttcattttg gggtgcttga tgaacaatta catcgtaata ggggctacag agatagatat    540

tacagtaact tagatattgc tccagcagca gatggttatg gattggcagg tttccctccg    600

gagcatagag cttggaggga agagccgtgg attcatcatg caccgccggg ttgtgggaat    660

gctccaagat catcgggatc caggaagaag cggagacagc gacgaagata ggtcgag       717
```

```
<210> SEQ ID NO 5
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Arg Lys Lys Arg Arg Gln Arg Arg Arg Leu Glu Asn Asp Asp Lys Leu
 1               5                  10                  15

Tyr Arg Ala Asp Ser Arg Pro Pro Asp Glu Ile Lys Gln Ser Gly Gly
            20                  25                  30

Leu Met Pro Arg Gly Gln Ser Glu Tyr Phe Asp Arg Gly Thr Gln Met
        35                  40                  45

Asn Ile Asn Leu Tyr Asp His Ala Arg Gly Thr Gln Thr Gly Phe Val
    50                  55                  60

Arg His Asp Asp Gly Tyr Val Ser Thr Ser Ile Ser Leu Arg Ser Ala
65                  70                  75                  80

His Leu Val Gly Gln Thr Ile Leu Ser Gly His Ser Thr Tyr Tyr Ile
                85                  90                  95

Tyr Val Ile Ala Thr Ala Pro Asn Met Phe Asn Val Asn Asp Val Leu
            100                 105                 110

Gly Ala Tyr Ser Pro His Pro Asp Glu Gln Glu Val Ser Ala Leu Gly
        115                 120                 125

Gly Ile Pro Tyr Ser Gln Ile Tyr Gly Trp Tyr Arg Val His Phe Gly
    130                 135                 140

Val Leu Asp Glu Gln Leu His Arg Asn Arg Gly Tyr Arg Asp Arg Tyr
145                 150                 155                 160

Tyr Ser Asn Leu Asp Ile Ala Pro Ala Ala Asp Gly Tyr Gly Leu Ala
                165                 170                 175

Gly Phe Pro Pro Glu His Arg Ala Trp Arg Glu Glu Pro Trp Ile His
            180                 185                 190

His Ala Pro Pro Gly Cys Gly Asn Ala Pro Arg Ser Ser Gly Ser Arg
        195                 200                 205

Lys Lys Arg Arg Gln Arg Arg Arg
    210                 215
```

```
<210> SEQ ID NO 6
<211> LENGTH: 258
<212> TYPE: PRT
<213> ORGANISM: Vibrio cholera

<400> SEQUENCE: 6

Met Val Lys Ile Ile Phe Val Phe Phe Ile Phe Leu Ser Ser Phe Ser
 1               5                  10                  15

Tyr Ala Asn Asp Asp Lys Leu Tyr Arg Ala Asp Ser Arg Pro Pro Asp
            20                  25                  30

Glu Ile Lys Gln Ser Gly Gly Leu Met Pro Arg Gly Gln Ser Glu Tyr
        35                  40                  45
```

-continued

```
Phe Asp Arg Gly Thr Gln Met Asn Ile Asn Leu Tyr Asp His Ala Arg
    50                  55                  60

Gly Thr Gln Thr Gly Phe Val Arg His Asp Asp Gly Tyr Val Ser Thr
65                  70                  75                  80

Ser Ile Ser Leu Arg Ser Ala His Leu Val Gly Gln Thr Ile Leu Ser
                85                  90                  95

Gly His Ser Thr Tyr Tyr Ile Tyr Val Ile Ala Thr Ala Pro Asn Met
            100                 105                 110

Phe Asn Val Asn Asp Val Leu Gly Ala Tyr Ser Pro His Pro Asp Glu
        115                 120                 125

Gln Glu Val Ser Ala Leu Gly Gly Ile Pro Tyr Ser Gln Ile Tyr Gly
    130                 135                 140

Trp Tyr Arg Val His Phe Gly Val Leu Asp Glu Gln Leu His Arg Asn
145                 150                 155                 160

Arg Gly Tyr Arg Asp Arg Tyr Tyr Ser Asn Leu Asp Ile Ala Pro Ala
                165                 170                 175

Ala Asp Gly Tyr Gly Leu Ala Gly Phe Pro Pro Glu His Arg Ala Trp
            180                 185                 190

Arg Glu Glu Pro Trp Ile His His Ala Pro Pro Gly Cys Gly Asn Ala
        195                 200                 205

Pro Arg Ser Ser Met Ser Asn Thr Cys Asp Glu Lys Thr Gln Ser Leu
    210                 215                 220

Gly Val Lys Phe Leu Asp Glu Tyr Gln Ser Lys Val Lys Arg Gln Ile
225                 230                 235                 240

Phe Ser Gly Tyr Gln Ser Asp Ile Asp Thr His Asn Arg Ile Lys Asp
                245                 250                 255

Glu Leu


<210> SEQ ID NO 7
<211> LENGTH: 86
<212> TYPE: PRT
<213> ORGANISM: Human immunodeficiency virus type 1

<400> SEQUENCE: 7

Met Glu Pro Val Asp Pro Arg Leu Glu Pro Trp Lys His Pro Gly Ser
 1               5                  10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Arg Ala His Gln Asn Ser Gln Thr
    50                  55                  60

His Gln Ala Ser Leu Ser Lys Gln Pro Thr Ser Gln Pro Arg Gly Asp
65                  70                  75                  80

Pro Thr Gly Pro Lys Glu
                85


<210> SEQ ID NO 8
<211> LENGTH: 9
<212> TYPE: PRT
<213> ORGANISM: Human immunodeficiency virus type 1

<400> SEQUENCE: 8

Arg Lys Lys Arg Arg Gln Arg Arg Arg
 1               5
```

```
<210> SEQ ID NO 9
<211> LENGTH: 27
<212> TYPE: DNA
<213> ORGANISM: Human immunodeficiency virus type 1

<400> SEQUENCE: 9

aggaagaagc ggagacagcg acgaaga                                          27


<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

gggcccctcg agaatgatga taagttatat cgg                                   33


<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11

cccgggggat cccgatgatc ttggagcatt ccc                                   33


<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12

tatgtttcca ccaagattag tttgaga                                          27


<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13

tctcaaacta atcttggtgg aaacata                                          27


<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14

cccgggcata tgaatgatga taagttatat cgg                                   33


<210> SEQ ID NO 15
<211> LENGTH: 33
<212> TYPE: DNA
```

-continued

```
<213> ORGANISM: Artificial Sequence
<220> FEATURE:
<223> OTHER INFORMATION: Description of Artificial Sequence: Synthetic
      primer

<400> SEQUENCE: 15

cccgggggat ccctacgatg atcttggagc att                               33


<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Ile Ile Asn Phe Glu Lys Leu
 1               5
```

A1 MOIETY OF CHOLERA TOXIN A SUBUNIT AS AN ADJUVANT FOR MUCOSAL AND SYSTEMIC VACCINES

CROSS REFERENCE TO PRIOR APPLICATION

This application claims priority pursuant to 35 U.S.C. §119 (e) to U.S. Provisional Patent Application No. 61/107,179, filed Oct. 21, 2008, which is hereby incorporated by reference in its entirety.

FIELD OF THE INVENTION

The present invention relates to cholera toxin subunit A1 (CTA1) protein fragments, adjuvant compositions, and methods relating to mucosal adjuvants for vaccines. The invention also relates to using recombinant CTA1 fragments conjugated to polypeptides containing a protein transduction domain as an immunomodulator.

BACKGROUND OF THE INVENTION

An important aspect of immune responses at mucosal surfaces is the production of secretory IgA (S-IgA) and its transport across the epithelium. This S-IgA response represents the first line of defense against the invasion by viral and bacterial pathogens. The mucosal immune system is an integrated network of tissues, cells and effector molecules which function to protect the host from those pathogens. Because of the presence of unique interconnected mucosal inductive and effector sites the mucosal immune system is separated from the peripheral immune system. Thus, the induction of peripheral immune responses by parenteral immunization does not result in significant mucosal immunity; however, mucosal immunization is capable of inducing protective immunity in both external secretions and peripheral immune compartments [2, 3].

The primary reason for using a mucosal route of vaccination is that most infections affect or start from a mucosal surface and that in these infections, topical application of a vaccine is often required to induce a protective immune response [1].

During work in the 1920s on the production of animal sera for human therapy, it was discovered that certain substances, notably aluminum salts, added to antigens greatly enhances antibody production—that is it acts as an adjuvant. Activation of innate immune responses is a prerequisite for an adjuvant function and a much needed component in any vaccine. Currently, a very limited spectrum of vaccine adjuvants are used commercially, with aluminum salts still being by far the largest group. With modern understanding of the process leading to triggering and the development of immunologic memory, considerable efforts have been made to produce better adjuvants (Immunology 7' th edition, 18-19, 2006, Ivan Roitt et al.).

Recently, much effort has been focused on inducing effective immune responses in mucosal tissues: however, most protein antigens (Ags) are rather weak immunogens when given via the mucosal route. In this regard, the coadministration of mucosal adjuvants, such as cholera toxin (CT), has been shown to effectively support Ag-specific mucosal immune responses. Thus, the development of effective and reliable mucosal adjuvants is a focus for a new generation of vaccines [3].

The CT contains 5 GM1 binding (B) subunits, an active (A1) subunit, and a bridging piece (A2) that links A1 to the 5B subunits. After it enters the cell, the A1 subunit enzymatically transfers ADP ribose from NAD to Gs protein, that regulates the adenylate cyclase system which is located on the inside of the plasma membrane of mammalian cells. The A1 fragment catalyzes the attachment of ADP-Ribose (ADPR) to the regulatory protein forming Gs-ADPR from which GTP cannot be hydrolyzed. Since GTP hydrolysis is the event that inactivates adenylate cyclase, the enzyme remains continually activated and stimulates adenylate cyclase, which results in the formation of large quantities of intracellular cyclic AMP (cAMP) [4].

The increase in cAMP often acts to immunomodulate many immune reactions such as enhanced antigen presentation by various antigen presenting cells (APCs) [5], promotion of isotype differentiation in B cells leading to increased IgA formation [6], and up-regulation of surface expression of CD80 and CD86 on the APC [7, 8].

CT is a strong systemic and mucosal adjuvant that greatly enhances IgG and IgA immune responses. Since the 1980s, the ability of CT to act as a mucosal adjuvant has been confirmed by a number of investigators with a variety of Ags [9]. The adjuvant properties of CT have been studied in a mouse model using both in vivo and in vitro experimental systems [10-13].

However, CT is a potent enterotoxin. For example, as little as 5 nanograms of purified CT administered orally is sufficient to induce significant diarrhea in humans, suggesting that enterotoxicity may seriously limit the practical use of CT [14].

Several studies were done to separate enterotoxicity from adjuvanticity. Mutants of CT have been constructed in attempts to dissociate the enterotoxic effects of these molecules from their adjuvant activity. Mutations in both the active site and the protease site of these two molecules have been examined and a number of different mutants of CT have been characterized [15-17].

A mutant CT (mCT; S61F and E112K) failed to induce adenosine diphosphate-ribosylation, cyclic adenosine monophosphate formation, or fluid accumulation in ligated ileal loops, and were thus nontoxic [18]. The mCT S61F also acts as a mucosal adjuvant by inducing CD41. Th2 cells secrete IL-4, IL-5, IL-6 and IL-10, which provide effective help for Ag-specific mucosal S-IgA, as well as serum IgG1, IgE and IgA Ab responses. Mucosal adjuvant activity of mCT S61F and E112K has been demonstrated using several Ags including ovalbumin, tetanus toxoid and influenza virus [18].

A fusion protein that combines the enzymatically active CTA1 with the Ig binding D region (DD) of staphylococcal protein A (CTA1-DD) was shown to augment specific serum as well as mucosal Ab responses to soluble protein Ags. CTA1-DD retains full enzymatic activity of the CTA1-subunit in a B cell-targeted fusion protein that lacks CTB and, thus, cannot bind to the GM1-ganglioside receptor [7, 19].

CTA1-DD was found to be completely non-toxic and, despite its more selective binding properties, had mucosal and systemic adjuvant effects comparable to that of intact CT (U.S. Pat. No. 5,917,026). However, the latter construct exhibits a selective cell binding moiety, DD (*Staphylococcus aureus* protein A binding site), aimed at directing the CTA1 moiety to cells expressing a receptor for DD, and specifically to subpopulations of B lymphocytes and dendritic cells. CTA1-DD was also shown to be highly immunogenic to CTA1 moiety and this enhancement of CTA1-specific serum Abs was essential to act as an immunoenhancing adjuvant (20)

Thus, there is a continuing need for more effective and reliable mucosal adjuvants for use in vaccines to produce mucosal and systemic immune effects.

SUMMARY OF THE INVENTION

In certain embodiments, the invention relates to a fusion protein comprising an A1 subunit of a bacterial enterotoxin selected from the group consisting of cholera toxin A1 and *Escherichia coli* heat-labile enterotoxin, conjugated at the amino terminus, carboxy terminus, or both amino and carboxy terminus with a polypeptide belonging to the class of protein transduction domains or cell-penetrating peptides.

In certain embodiments, the fusion protein is capable of augmenting an immune response to a co-administered antigen.

In additional embodiments, the enterotoxin comprises a subunit with ADP ribosyl transferase activity. In certain embodiments the subunit is the ADP-ribosylating A1 subunit of cholera toxin.

In additional embodiments, the enterotoxin comprises an ADP-ribosylating A1 subunit of *Escherichia coli* heat-labile enterotoxin.

In yet additional embodiments, the protein transduction domain or cell-penetrating peptide is the HIV-1 Tat protein transduction domain.

In yet further embodiments, the invention relates to an isolated polypeptide comprising an amino acid sequence of SEQ ID NO:5.

In yet additional embodiments, the invention relates to vaccine composition comprising any of the fusion or recombinant proteins described herein.

In additional embodiments the invention relates to a vaccine composition comprising a) the fusion protein or polypeptide described herein, b) an antigen, and c) a pharmaceutically acceptable carrier or diluent, wherein the amounts of a) and b) in combination are effective to elicit an immune response. In certain embodiments, the vaccine is administered by a mucosal or a systemic route. In yet additional embodiments, the vaccine is capable of inducing a mucosal immune response.

In certain embodiments, the mucosal immune response is a secretory antibody response. In yet additional embodiments, the mucosal immune response is a cytotoxic T lymphocyte response.

In yet additional embodiments, the vaccine is capable of inducing a systemic immune response. In certain embodiments, the systemic immune response is a serum antibody response. In yet additional embodiments, the systemic immune response is a cytotoxic T lymphocyte response.

In additional embodiments the invention relates to an isolated nucleic acid fragment encoding any of the polypeptides described herein.

In yet additional embodiments, the invention relates to a host cell transformed with any of the nucleic acids described herein.

In yet additional embodiments, the invention relates to an expression vector comprising any of the nucleic acids described herein.

In yet additional embodiments, the invention relates to a method for producing a fusion polypeptide comprising culturing any of the host cells as described herein, under suitable conditions for protein expression.

In yet additional embodiments, the invention relates to an immunogenic composition comprising any of the fusion proteins or, b) an antigen, and optionally c) a pharmaceutically acceptable carrier or diluent, wherein the amounts of a) and b) in combination are effective to elicit an immune response.

In yet additional embodiments, the invention relates to a kit comprising the vaccine or immunogenic compositions described herein.

In yet additional embodiments, the invention relates to a kit comprising the fusion protein or polypeptide described herein.

In yet additional embodiments, the invention relates to a method of treating a mammal suffering from or susceptible to a pathogenic enteric infection, comprising administering an effective amount of any of the vaccine or immunogenic compositions described herein.

In yet additional embodiments, the invention relates to a method for modulating the immune response of a mammal comprising administering an effective amount of the any of the vaccine or immunogenic compositions described herein.

The amounts of the fusion protein or polypeptide adjuvants as described herein may be present in a vaccine or immunogenic composition in amounts ranging from about 1 μg to 1 milligram per dose. In certain embodiments, the vaccine comprising the adjuvant is given on multiple occasions, such as 2 to 3 occasions starting on day 0 and then re-administered on day 14 to 28, and if necessary again 1 to 6 months after the second administration. To maintain a sufficient level of immunological memory, the vaccine containing the adjuvant may be given 1 year and up to several years after the last vaccination.

These and other aspects of the present invention will be apparent to those of ordinary skill in the art in light of the present descriptions, claims and drawings.

BRIEF DESCRIPTION OF THE DRAWINGS

FIG. 2 shows OVA-specific serum IgG responses of mice immunized nasally with TCTA1T, TmCTA1T or CT as an adjuvant. Groups of 5 mice were immunized nasally on days 0, 14, 28, with 20 μg of OVA alone, with 10 μg of TCTA1T, TmCTA1T or 2 μg of CT. Serum samples were collected on days 13, 27, 41.

FIG. 3 shows OVA-specific mucosal antibody responses of mice immunized nasally with TCTA1T, TmCTA1T or CT as an adjuvant. Saliva was collected on days 13, 27, 41. Lung tissue, lung wash, and nasal wash samples were collected on day 14 after the third immunization.

FIG. 6 shows OVA-specific CD8+ cytotoxic T cell response in spleen and lung of mice immunized nasally with TCTA1T, TmCTA1T or CT.

FIG. 8 shows in vitro and in vivo toxicity of TCTA1, TmCTA1 or CT through cAMP test, footpad edema, and intestinal loop test.

FIG. 10A-C show OVA-specific antibody responses of mice immunized nasally with CTA1 as an adjuvant. Serum (FIG. 10A) and saliva (FIG. 10B) were collected on days 13, 27, 41. Lung tissue (FIG. 10C) was collected on day 14 after the third immunization.

FIG. 12. shows OVA-specific CD8+ cytotoxic T cell response in spleen and lung of mice immunized nasally with CTA1 plus OVA.

FIG. 13A-C show in vitro and in vivo toxicity of CTA1 through cAMP test (FIG. 13A), footpad edema (FIG. 13B), and intestinal loop test (FIG. 13C).

FIGS. 14A-D show nucleotide sequences of cholera toxin A sequence (FIG. 14A), pET15b-CTA1 (FIG. 14B), pET15b-TCTA1T, and pET15b-TmCTXA1T (FIG. 14D).

FIGS. 15A-C show amino acid sequences of TCTA1T (an embodiment of PTD-CTA1-PTD, also referred to as SEQ ID NO:5) (FIG. 15A), CTA1 (FIG. 15B), and HIV Tat, showing the PTD motif in bold (FIG. 15C).

FIGS. 16A-B show that TCTAIT does not elicit antibodies directed against itself.

DETAILED DESCRIPTION

Figures 1A, 1B:
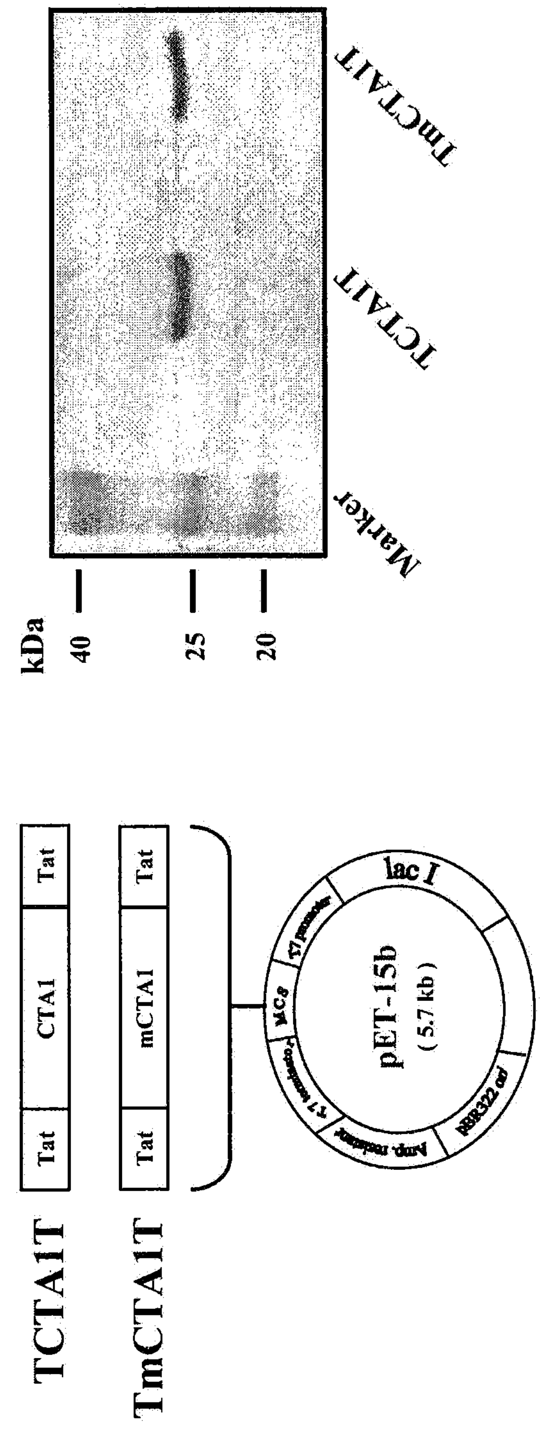
FIGS. 1A-B show a schematic representation of PTD CTA1 fusion protein (TCTA1T) expression vectors (FIG. 1A) and purification of the TCTA1T protein from *E. coli* (FIG. 1B).

The present invention relates to cholera toxin CTA1 protein fragments, adjuvant compositions, and methods relating to mucosal adjuvants for vaccines. The invention also relates to using recombinant CTA1 fragments as immunomodulatory agents.

Cholera toxin (CT) is a potent mucosal adjuvant and one of the most widely used mucosal adjuvant in animal models, but unfortunately very toxic to use as an adjuvant for mucosal vaccines in humans. CT consists of A1, A2, and B subunits. The A1 subunit (CTA1) has adjuvant activity and the B subunit (CTB) binds to cell membranes via the GM1 ganglioside receptors on all nucleated cells. The sequence of the CT was described by Mekalanos, J. J., et al., Nature, 306, 551-557 (1983).

After binding, CTA1 is translocated into the cell, and then induces a cascade of events which increase cAMP level that finally results in secretion of chloride and water with subsequent diarrhea. A new approach to develop a safe and effective mucosal adjuvant from cholera toxin by replacing the CTB subunit with a protein transduction domain (PTD) which lowers toxicity but having a potent adjuvant activity, has been developed as described herein. To enhance the cellular uptake, PTD was attached (i.e. fused) at both N- and C-termini of CTA1. Unlike CT, this fusion protein can enter into the cell without binding to cell membrane receptors and CTA1 might be localized at a different site from CTA1 delivered by CTB. The toxicity and adjuvant activity of PTD CTA1 fusion protein, embodiments of which will be referred to hereafter as TCTA1T, or PTD-CTA1-PTD, or SEQ ID NO:5, was compared with CT by co-administration with ovalbumin. Here, it was found that TCTA1T enhances sIgA and IgG antibody responses which are comparable to that of CT. TCTA1T generated roughly 5-times (IgG class) or 10-times (IgA class) as many antibody-secreting cells (ASCs) in the lungs than that of CT. The in vivo CTL activity elicited by the TCTA1T was slightly lower than that of the CT but still much higher than that of the mutant TmCTA1T which has inactive with respect to ADP ribosyltransferase activity and that of OVA administered alone. Moreover, co-administration of influenza M2 protein with TCTA1T resulted in complete protection against a lethal challenge with live H1N1 virus. Further, and in contrast to CT, TCTA1T did not cause foot pad edema and failed to induce fluid loss in a small intestinal loop assay. CTA1 devoid of PTD extension also showed adjuvant activity by enhancing serum IgG, secretory IgA responses, and expansion of antibody-secreting cells in the lung and spleen without exhibiting toxicity in mice. These results indicate that TCTA1T and CTA1 have substantial adjuvant activity but, contrary to CT, appear to be devoid of toxicity and could thus be useful as safe and effective mucosal adjuvants.

The identification of a class of peptides, called cell-penetrating peptides or protein transduction domains (PTD) within small regions of proteins, with a capacity to cross biological membranes has permitted to increase the intracellular bioavailability of macromolecules with low cell penetrance by conjugating these macromolecules to said PTDs [21, 22]. Because of their ability to cross the plasma membrane, these PTDs provide powerful tools for studying the cellular functions of proteins and increase the potential clinical applications of proteins. In addition, PTDs as carriers are being extended to other macromolecules, including nucleic acid, nanoparticles, and liposomes [23-26]. It has also been found that these PTDs direct the entry of conjugated macromolecules into cells most often, but not always through an endosomal pathway which does not deliver these macromolecules to the cytoplasm and/or the nucleus.

The PTD responsible for efficient delivery of the HIV Tat is a highly basic internal domain, Tat (49-57) (RKKRRQRRR (SEQ ID NO: 8)). HIV-1 Tat PTD is able to cross the plasma membrane of cells either alone or fused to full length proteins or peptides. It has been suggested that transduction by HIV-1 Tat PTD does not occur in a classical receptor, transporter or endosome-mediated fashions.

The GFP fusion protein with PTD at its C-terminus was taken up as efficiently as the GFP fusion protein fused by PTD at its N-terminus whereas the presence of PTD at both termini resulted in enhanced uptake [27].

CTA1 is a 22-kDa ADP ribosyltransferase with three distinct subdomains: CTA11 (residues 1 to 132) comprises the catalytic core of the toxin; CTA12 (residues 133 to 161) is a short, flexible subdomain; and CTA13 (residues 162 to 192) is a globular region that interfaces with CTA11 and has many hydrophobic residues and a single cysteine residue that provides the disulfide linkage to CTA2. The CTA1 amino acid sequence has been described and is listed as EU487781 and also as GenBank ID (GI:169247721) amino acid from 19 to 212. The 5.5-kDa CTA2 polypeptide maintains numerous noncovalent interactions with the B moiety and thereby acts as a linker between the catalytic and cell-binding components of CT. The homopentameric B moiety of CT is assembled from 11.6-kDa monomers, binds to GM1 gangliosides on the eukaryotic plasma membrane, and serves as a vehicle for CTA1 delivery to the endoplasmic reticulum (ER).

Cholera toxin (CT) moves from the plasma membrane to the endoplasmic reticulum (ER) by retrograde vesicular traffic. In the ER, the catalytic CTA1 polypeptide dissociates from the rest of the toxin and enters the cytosol by a process that involves the quality control mechanism of ER-associated degradation (ERAD). The cytosolic CTA1 then ADP ribosylates Gs, resulting in adenylate cyclase activation and intoxication of the target cell. It is hypothesized that the C-terminal A13 subdomain of CTA1 plays two crucial roles in the intoxication process: (i) it contains a hydrophobic domain that triggers the ERAD mechanism and (ii) it facilitates interaction with the cytosolic ADP-ribosylation factors (ARFs) that serve as allosteric activators of CTA1 [28].

Based on these results, the present inventors developed a safe adjuvant with an ADP ribosyl transferase activity, even after it enters the epithelial cells since the fusion TCTA1T enters the cell using a different pathway from native CT. In certain embodiments, the invention relates to using PTD CTA1 fusion protein (TCTA1T) as an adjuvant. In additional embodiments, the invention relates to using CTA1 as an adjuvant in the form of a recombinant protein delivered as a free or non-conjugated protein, or expressed by a live-attenuated recombinant virus, a live-attenuated bacteria, or a virus-like particle.

In other embodiments, the invention relates to the use of polypeptides with ADP ribosyl transferase activity, such as *Escherichia coli* A1 subunit of heat-labile enterotoxin.

The TCTA1T recombinant protein consists of CTA1 and HIV Tat PTD at both N- and C-termini of CTA1. This molecule enters into the living cells nonspecifically without binding to cell membrane receptors, transporters or endosome-mediated delivery. Therefore, the CTA1 moiety from TCTA1T is expected to be localized at different subcellular site from CTA1 of CT which uses ganglioside GM1 receptors for receptor mediated endocytosis.

The results demonstrate that TCTA1T has strong adjuvant activities without any toxicity in mice.

In certain embodiments, the invention relates to the generation of mucosal adjuvants for use in vaccines. The present data show that TCTA1T enhances sIgA and IgG antibody response, ASCs and CTL activity. TCTA1T also provides protection against subsequent lethal virus challenge.

The results described herein also demonstrate that CTA1 lacking CTB for ganglioside GM1 receptor binding has strong adjuvant activities without any toxicity in mice. CTA1 enhances sIgA and IgG antibody response, ASCs and CTL activity.

The invention is also directed toward using CTA1 as an immunomodulator in a form of a recombinant protein, virus and/or bacteria.

In accordance with the present invention there may be numerous tools and techniques within the skill of the art, such as those commonly used in molecular immunology, cellular immunology, pharmacology, and microbiology. Such tools and techniques are described in detail in e.g., Sambrook et al. (2001) Molecular Cloning: A Laboratory Manual. 3rd ed. Cold Spring Harbor Laboratory Press: Cold Spring Harbor, N.Y.; Ausubel et al. eds. (2005) Current Protocols in Molecular Biology. John Wiley and Sons, Inc.: Hoboken, N.J.; Bonifacino et al. eds. (2005) Current Protocols in Cell Biology. John Wiley and Sons, Inc.: Hoboken, N.J.; Coligan et al. eds. (2005) Current Protocols in Immunology, John Wiley and Sons, Inc.: Hoboken, N.J.; Coico et al. eds. (2005) Current Protocols in Microbiology, John Wiley and Sons, Inc.: Hoboken, N.J.; Coligan et al. eds. (2005) Current Protocols in Protein Science, John Wiley and Sons, Inc.: Hoboken, N.J.; and Enna et al. eds. (2005) Current Protocols in Pharmacology, John Wiley and Sons, Inc.: Hoboken, N.J.

The abbreviations in the specification correspond to units of measure, techniques, properties or compounds as follows: "min" means minutes, "h" means hour(s), "μL" means microliter(s), "mL" means milliliter(s), "mM" means millimolar, "M" means molar, "mmole" means millimole(s), "kb" means kilobase, "bp" means base pair(s), and "IU" means International Units.

"Polymerase chain reaction" is abbreviated PCR; "Reverse transcriptase polymerase chain reaction" is abbreviated RT-PCR; "Untranslated region" is abbreviated UTR; "Sodium dodecyl sulfate" is abbreviated SDS; and "High Pressure Liquid Chromatography" is abbreviated HPLC.

"Amplification" of DNA as used herein denotes the use of polymerase chain reaction (PCR) to increase the concentration of a particular DNA sequence within a mixture of DNA sequences. For a description of PCR see Saiki et al., Science 1988, 239:487.

A "polynucleotide" or "nucleotide sequence" is a series of nucleotide bases (also called "nucleotides") in a nucleic acid, such as DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and anti-sense polynucleotide (although only sense stands are being represented herein). This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases, for example thio-uracil, thio-guanine and fluoro-uracil.

The nucleic acids herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

The term "nucleic acid hybridization" refers to anti-parallel hydrogen bonding between two single-stranded nucleic acids, in which A pairs with T (or U if an RNA nucleic acid) and C pairs with G. Nucleic acid molecules are "hybridizable" to each other when at least one strand of one nucleic acid molecule can form hydrogen bonds with the complementary bases of another nucleic acid molecule under defined stringency conditions. Stringency of hybridization is determined, e.g., by (i) the temperature at which hybridization and/or washing is performed, and (ii) the ionic strength and (iii) concentration of denaturants such as formamide of the hybridization and washing solutions, as well as other parameters. Hybridization requires that the two strands contain substantially complementary sequences. Depending on the stringency of hybridization, however, some degree of mismatches may be tolerated. Under "low stringency" conditions, a greater percentage of mismatches are tolerable (i.e., will not prevent formation of an anti-parallel hybrid). See *Molecular Biology of the Cell*, Alberts et al., 3rd ed., New York and London: Garland Publ., 1994, Ch. 7.

Typically, hybridization of two strands at high stringency requires that the sequences exhibit a high degree of complementarity over an extended portion of their length. Examples of high stringency conditions include: hybridization to filter-bound DNA in 0.5 M NaHPO4, 7% SDS, 1 mM EDTA at 65° C., followed by washing in 0.1×SSC/0.1% SDS at 68° C. (where 1×SSC is 0.15M NaCl, 0.15M Na citrate) or for oligonucleotide molecules washing in 6×SSC/0.5% sodium pyrophosphate at about 37° C. (for 14 nucleotide-long oligos), at about 48° C. (for about 17 nucleotide-long oligos), at about 55° C. (for 20 nucleotide-long oligos), and at about 60° C. (for 23 nucleotide-long oligos)). Accordingly, the term "high stringency hybridization" refers to a combination of solvent and temperature where two strands will pair to form a "hybrid" helix only if their nucleotide sequences are almost perfectly complementary (see *Molecular Biology of the Cell*, Alberts et al., 3rd ed., New York and London: Garland Publ., 1994, Ch. 7).

Conditions of intermediate or moderate stringency (such as, for example, an aqueous solution of 2×SSC at 65° C.; alternatively, for example, hybridization to filter-bound DNA in 0.5 M NaHPO4, 7% SDS, 1 mM EDTA at 65° C., and washing in 0.2×SSC/0.1% SDS at 42° C.) and low stringency (such as, for example, an aqueous solution of 2×SSC at 55° C.), require correspondingly less overall complementarity for hybridization to occur between two sequences. Specific temperature and salt conditions for any given stringency hybridization reaction depend on the concentration of the target DNA and length and base composition of the probe, and are normally determined empirically in preliminary experiments, which are routine (see Southern, *J. Mol. Biol.* 1975; 98: 503; Sambrook et al., *Molecular Cloning: A Laboratory Manual,* 2nd ed., vol. 2, ch. 9.50, CSH Laboratory Press, 1989; Ausubel et al. (eds.), 1989*, Current Protocols in Molecular Biology*, Vol. I, Green Publishing Associates, Inc., and John Wiley & Sons, Inc., New York, at p. 2.10.3).

As used herein, the term "standard hybridization conditions" refers to hybridization conditions that allow hybridization of sequences having at least 75% sequence identity. According to a specific embodiment, hybridization conditions of higher stringency may be used to allow hybridization of only sequences having at least 80% sequence identity, at least 90% sequence identity, at least 95% sequence identity, or at least 99% sequence identity.

Nucleic acid molecules that "hybridize" to any desired nucleic acids of the present invention may be of any length. In one embodiment, such nucleic acid molecules are at least 10, at least 15, at least 20, at least 30, at least 40, at least 50, and at least 70 nucleotides in length. In another embodiment, nucleic acid molecules that hybridize are of about the same length as the particular desired nucleic acid.

As used herein, the term "isolated" means that the referenced material is removed from the environment in which it is normally found. Thus, an isolated biological material can be free of cellular components, i.e., components of the cells in which the material is found or produced. Isolated nucleic acid molecules include, for example, a PCR product, an isolated mRNA, a cDNA, or a restriction fragment. Isolated nucleic acid molecules also include, for example, sequences inserted into plasmids, cosmids, artificial chromosomes, and the like. An isolated nucleic acid molecule is preferably excised from the genome in which it may be found, and more preferably is no longer joined to non-regulatory sequences, non-coding sequences, or to other genes located upstream or downstream of the nucleic acid molecule when found within the genome. An isolated protein may be associated with other proteins or nucleic acids, or both, with which it associates in the cell, or with cellular membranes if it is a membrane-associated protein.

"Treating" or "treatment" of a state, disorder or condition includes:

(1) preventing or delaying the appearance of clinical or sub-clinical symptoms of the state, disorder or condition developing in a mammal that may be afflicted with or predisposed to the state, disorder or condition but does not yet experience or display clinical or subclinical symptoms of the state, disorder or condition; or
(2) inhibiting the state, disorder or condition, i.e., arresting, reducing or delaying the development of the disease or a relapse thereof (in case of maintenance treatment) or at least one clinical or sub-clinical symptom thereof; or
(3) relieving the disease, i.e., causing regression of the state, disorder or condition or at least one of its clinical or sub-clinical symptoms.

The benefit to a subject to be treated is either statistically significant or at least perceptible to the patient or to the physician.

An "immune response" refers to the development in the host of a cellular and/or antibody-mediated immune response to a composition or vaccine of interest. Such a response usually consists of the subject producing antibodies, B cells, helper T cells, and/or cytotoxic T cells directed specifically to an antigen or antigens included in the composition or vaccine of interest. The immune response also may include regulatory T-cells, whose activity is beyond the organism of interest, and may suppress other immune or allergic responses.

A "therapeutically effective amount" means the amount of a compound, adjuvant, or vaccine composition that, when administered to a mammal for treating a state, disorder or condition, is sufficient to effect such treatment. The "therapeutically effective amount" will vary depending on the compound, bacteria or analogue administered as well as the disease and its severity and the age, weight, physical condition and responsiveness of the mammal to be treated.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

While it is possible to use a composition provided by the present invention for therapy as is, it may be preferable to administer it in a pharmaceutical formulation, e.g., in admixture with a suitable pharmaceutical excipient, diluent or carrier selected with regard to the intended route of administration and standard pharmaceutical practice. Accordingly, in one aspect, the present invention provides a pharmaceutical composition or formulation comprising at least one active composition, or a pharmaceutically acceptable derivative thereof, in association with a pharmaceutically acceptable excipient, diluent and/or carrier. The excipient, diluent and/or carrier must be "acceptable" in the sense of being compatible with the other ingredients of the formulation and not deleterious to the recipient thereof.

The compositions of the invention can be formulated for administration in any convenient way for use in human or veterinary medicine. The invention therefore includes within its scope pharmaceutical compositions comprising a product of the present invention that is adapted for use in human or veterinary medicine.

In a preferred embodiment, the pharmaceutical composition is conveniently administered as a liquid oral formulation. Although there are no physical limitations to delivery of the formulation, oral delivery is preferred because of its ease and convenience, and because oral formulations readily accommodate additional mixtures, such as milk, yogurt, and infant formula. Other oral dosage forms are well known in the art and include tablets, caplets, gelcaps, capsules, and medical foods. Tablets, for example, can be made by well-known compression techniques using wet, dry, or fluidized bed granulation methods.

Such oral formulations may be presented for use in a conventional manner with the aid of one or more suitable excipients, diluents, and carriers. Pharmaceutically acceptable excipients assist or make possible the formation of a dosage form for a bioactive material and include diluents, binding agents, lubricants, glidants, disintegrants, coloring agents, and other ingredients. Preservatives, stabilizers, dyes and even flavoring agents may be provided in the pharmaceutical composition. Examples of preservatives include sodium benzoate, ascorbic acid and esters of p-hydroxybenzoic acid. Antioxidants and suspending agents may be also used. An excipient is pharmaceutically acceptable if, in addition to performing its desired function, it is non-toxic, well tolerated upon ingestion, and does not interfere with absorption of bioactive materials.

Acceptable excipients, diluents, and carriers for therapeutic use are well known in the pharmaceutical art, and are described, for example, in Remington: The Science and Practice of Pharmacy. Lippincott Williams & Wilkins (A. R. Gennaro edit. 2005). The choice of pharmaceutical excipient, diluent, and carrier can be selected with regard to the intended route of administration and standard pharmaceutical practice.

As used herein, the phrase “pharmaceutically acceptable” refers to molecular entities and compositions that are generally regarded as physiologically tolerable.

“Patient” or “subject” refers to mammals and includes human and veterinary subjects.

The dosage of an adjuvant formulation or vaccine composition containing the CTA1 adjuvant will vary widely, depending upon the nature of the disease, the patient’s medical history, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered daily, semi-weekly, etc., to maintain an effective dosage level.

The term “carrier” refers to a diluent, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in “Remington’s Pharmaceutical Sciences” by E. W. Martin.

The invention also encompasses pharmaceutical compositions and vaccines. The pharmaceutical compositions and vaccine compositions of the invention comprise at least one of the novel *Shigella* antigens, and one or more adjuvants along with a pharmaceutically acceptable carrier or excipient. Methods of formulating pharmaceutical compositions and vaccines are well-known to those of ordinary skill in the art, as described in Remington’s, supra.

Formulations.

The compositions of the present invention may comprise pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hylauronic acid may also be used. See, e.g., Remington’s Pharmaceutical Sciences, 18th Ed. (1990, Mack Publishing Co., Easton, Pa. 18042) pages 1435-1712 which are herein incorporated by reference.

Contemplated for use herein are oral solid dosage forms, which are described generally in *Remington’s Pharmaceutical Sciences,* 18th Ed. 1990 (Mack Publishing Co. Easton Pa. 18042) at Chapter 89, which is herein incorporated by reference. Solid dosage forms include tablets, capsules, pills, troches or lozenges, cachets, pellets, powders, or granules. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (e.g., U.S. Pat. No. 5,013,556). A description of possible solid dosage forms for the therapeutic is given by Marshall, K. In: *Modern Pharmaceutics* Edited by G. S. Banker and C. T. Rhodes Chapter 10, 1979, herein incorporated by reference. In general, the formulation will include the therapeutic agent and inert ingredients which allow for protection against the stomach environment, and release of the biologically active material in the intestine.

Also contemplated for use herein are liquid dosage forms for oral administration, including pharmaceutically acceptable emulsions, solutions, suspensions, and syrups, which may contain other components including inert diluents; adjuvants, wetting agents, emulsifying and suspending agents; and sweetening, flavoring, coloring, and perfuming agents.

For oral formulations, the location of release may be the stomach, the small intestine (the duodenum, the jejunum, or the ileum), the large intestine, or the buccal mucosa. One skilled in the art has available formulations which will not dissolve in the stomach, yet will release the material in the duodenum or elsewhere in the intestine, e.g., by the use of an enteric coating. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (i.e. powder), for liquid forms a soft gelatin shell may be used. The shell material of cachets could be thick starch or other edible paper. For pills, lozenges, molded tablets or tablet triturates, moist massing techniques can be used. The formulation of the material for capsule administration could also be as a powder, lightly compressed plugs, or even as tablets. These therapeutics could be prepared by compression.

One may dilute or increase the volume of the therapeutic agent with an inert material. These diluents could include carbohydrates, especially mannitol, □-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic agent into a solid dosage form. Materials used as disintegrates include but are not limited to starch, including the commercial disintegrant based on starch, Explotab, Sodium starch glycolate, Amberlite, sodium carboxymethylcellulose, ultramylopectin, sodium alginate, gelatin, orange peel, acid carboxymethyl cellulose, natural sponge and bentonite may all be used. The disintegrants may also be insoluble cationic exchange resins. Powdered gums may be used as disintegrants and as binders. and can include powdered gums such as agar, Karaya or tragacanth. Alginic acid and its sodium salt are also useful as disintegrants. Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the peptide (or derivative).

An antifrictional agent may be included in the formulation to prevent sticking during the formulation process. Lubricants may be used as a layer between the peptide (or derivative) and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties drug during formulation and to aid rearrangement during compression might be added. The glidants may include starch, talc, pyrogenic silica and hydrated silicoaluminate.

To aid dissolution of the therapeutic agent into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the protein or derivative either alone or as a mixture in different ratios.

Controlled release oral formulations may used in practicing the present invention. The therapeutic agent could be incorporated into an inert matrix which permits release by either diffusion or leaching mechanisms, e.g., gums. Slowly degenerating matrices may also be incorporated into the formulation. Some enteric coatings also have a delayed release effect. Another form of a controlled release is by a method based on the Oros therapeutic system (Alza Corp.), i.e. the therapeutic agent is enclosed in a semipermeable membrane which allows water to enter and push agent out through a single small opening due to osmotic effects.

Other coatings may be used for the formulation. These include a variety of sugars which could be applied in a coating pan. The therapeutic agent could also be given in a film coated tablet and the materials used in this instance are divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxy-methyl cellulose, providone and the polyethylene glycols. The second group consists of the enteric materials that are commonly esters of phthalic acid. A mix of materials might be used to provide the optimum film coating. Film coating may be carried out in a pan coater or in a fluidized bed or by compression coating.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants, preserving, wetting, emulsifying, and dispersing agents. The pharmaceutical compositions may be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Vaccines.

In the case of vaccines, it is often observed that a primary challenge with an antigen alone, in the absence of an adjuvant, will fail to elicit a humoral or cellular immune response. Therefore the vaccines of the invention may contain additional adjuvants including, but not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, and potentially useful human adjuvants such as N-acetyl-muramyl-L-threonyl-D-isoglutamine (thr-MDP), N-acetyl-nor-muramyl-L-alanyl-D-isoglutamine, N-acetyl-muramyl-L-alanyl-D-isoglutaminyl-L-alanine-2-(1'-2'-dipalmitoyl-sn-glycero-3-hydroxyphosphoryloxy)-ethylamine, BCG (bacille Calmette-Guerin) and *Corynebacterium parvum*. An adjuvant can serve as a tissue depot that slowly releases the antigen and also as a lymphoid system activator that non-specifically enhances the immune response (Hood et al., *Immunology, Second Ed.,* 1984, Benjamin/Cummings: Menlo Park, Calif., p. 384). Where the vaccine is intended for use in human subjects, the adjuvant should be pharmaceutically acceptable.

Administration.

Such pharmaceutical compositions or vaccines may be for administration by oral (solid or liquid), parenteral (intramuscular, intraperitoneal, intravenous (IV) or subcutaneous injection), transdermal (either passively or using iontophoresis or electroporation), transmucosal (nasal, vaginal, rectal, or sublingual), or inhalation routes of administration, or using bioerodible inserts and can be formulated in dosage forms appropriate for each route of administration.

In certain embodiments, the compositions or vaccines are administered by pulmonary delivery. The composition or vaccine is delivered to the lungs of a mammal while inhaling and traverses across the lung epithelial lining to the blood stream [see, e.g., Adjei, et al. Pharmaceutical Research 1990; 7:565-569; Adjei, et al. Int. J. Pharmaceutics 1990; 63:135-144 (leuprolide acetate); Braquet, et al. J. Cardiovascular Pharmacology 1989; 13 (sup 5):143-146 (endothelin-1); Hubbard, et al. (1989) Annals of Internal Medicine, Vol. III, pp. 206-212 (α1-antitrypsin); Smith, et al. J. Clin. Invest. 1989; 84:1145-1146 (α-1-proteinase); Oswein, et al. "Aerosolization of Proteins", 1990; Proceedings of Symposium on Respiratory Drug Delivery II Keystone, Colo. (recombinant human growth hormone); Debs, et al. J. Immunol. 1988; 140:3482-3488 (interferon-γ and tumor necrosis factor α); and U.S. Pat. No. 5,284,656 to Platz, et al. (granulocyte colony stimulating factor). A method and composition for pulmonary delivery of drugs for systemic effect is described in U.S. Pat. No. 5,451,569 to Wong, et al. See also U.S. Pat. No. 6,651,655 to Licalsi et al.

Contemplated for use in the practice of certain embodiments of the invention are a wide range of mechanical devices designed for pulmonary delivery of therapeutic products, including but not limited to nebulizers, metered dose inhalers, and powder inhalers, all of which are familiar to those skilled in the art. Some specific examples of commercially available devices suitable for the practice of this invention are the Ultravent nebulizer (Mallinckrodt Inc., St. Louis, Mo.); the Acorn II nebulizer (Marquest Medical Products, Englewood, Colo.); the Ventolin metered dose inhaler (Glaxo Inc., Research Triangle Park, N.C.); and the Spinhaler powder inhaler (Fisons Corp., Bedford, Mass.). All such devices require the use of formulations suitable for the dispensing of the therapeutic agent. Typically, each formulation is specific to the type of device employed and may involve the use of an appropriate propellant material, in addition to the usual diluents, adjuvants, surfactants and/or carriers useful in therapy. Also, the use of liposomes, microcapsules or microspheres, inclusion complexes, or other types of carriers is contemplated.

Formulations for use with a metered-dose inhaler device will generally comprise a finely divided powder containing the therapeutic agent suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing the therapeutic agent, and may also include a bulking agent, such as lactose, sorbitol, sucrose, or mannitol in amounts which facilitate dispersal of the powder from the device, e.g., 50 to 90% by weight of the formulation. The therapeutic agent should most advantageously be prepared in particulate form with an average particle size of less than 10 mm (or microns), most preferably 0.5 to 5 mm, for most effective delivery to the distal lung.

Nasal or other mucosal delivery of the therapeutic agent is also contemplated. Nasal delivery allows the passage to the blood stream directly after administering the composition to the nose, without the necessity for deposition of the product in the lung. Formulations for nasal delivery include those with dextran or cyclodextran and saponin as an adjuvant.

The composition or vaccine of the present invention may be administered in conjunction with one or more additional active ingredients, pharmaceutical compositions, or vaccines. The therapeutic agents of the present invention may be administered to an animal, preferably a mammal, most preferably a human.

Dosages

Following methodologies which are well-established in the art, effective doses and toxicity of the compounds and compositions of the instant invention, which performed well in in vitro tests, are then determined in preclinical studies using small animal models (e.g., mice or rats) in which the *Shigella* antigens, polypeptide, pharmaceutical, or vaccine compositions have been found to be therapeutically effective and in which these drugs can be administered by the same route proposed for the human clinical trials.

For any pharmaceutical composition used in the methods of the invention, the therapeutically effective dose can be estimated initially from animal models. Dose-response curves derived from animal systems are then used to determine testing doses for the initial clinical studies in humans. In safety determinations for each composition, the dose and frequency of administration should meet or exceed those anticipated for use in the clinical trial.

As disclosed herein, the dose of the components in the compositions of the present invention is determined to ensure that the dose administered continuously or intermittently will not exceed an amount determined after consideration of the results in test animals and the individual conditions of a patient. A specific dose naturally varies depending on the dosage procedure, the conditions of a patient or a subject animal such as age, body weight, sex, sensitivity, feed, dosage period, drugs used in combination, and seriousness of the disease. The appropriate dose and dosage times under certain conditions can be determined by the test based on the above-described indices but may be refined and ultimately decided according to the judgment of the practitioner and each patient's circumstances (age, general condition, severity of symptoms, sex, etc.) according to standard clinical techniques.

Toxicity and therapeutic efficacy of the compositions of the invention can be determined by standard pharmaceutical procedures in experimental animals, e.g., by determining the $LD_{50}$ (the dose lethal to 50% of the population) and the $ED_{50}$ (the dose therapeutically effective in 50% of the population). The dose ratio between therapeutic and toxic effects is the therapeutic index and it can be expressed as the ratio $ED_{50}/LD_{50}$. Compositions that exhibit large therapeutic indices are preferred.

The data obtained from animal studies can be used in formulating a range of doses for use in humans. The therapeutically effective doses of in humans lay preferably within a range of circulating concentrations that include the $ED_{50}$ with little or no toxicity. The dosage can vary within this range depending upon the dosage form employed and the route of administration utilized. Ideally, a single dose of each drug should be used daily.

The following describes materials and methods employed in Examples 1-9.

Materials and Methods

Construction of Plasmids Expressing TCTA1T and TmCTA1T Proteins

Plasmid expressing GFP protein with HIV-1 Tat PTD (amino acids 49-57 of the TAT sequence, RKKRRQRRR (SEQ ID NO: 8); nucleotide sequence: AGGAAGAAGCGGAGACAGCGACGAAGA (SEQ ID NO: 9)) at both N- and C-terminus (pET15b-Tat-GFP-Tat) was provided by Dr. Soo Young Choi from Hallym University, Korea. A DNA encoding cholera toxin A1 subunit (amino acid 1-194) was amplified by PCR using a forward primer (5'-GGGCCCCTCGAGAATGATGATAAGTTATATCGG-3' (SEQ ID NO: 10)) and a reverse primer (5'-CCCGGGGGATCCCGATGATCTTGGAGCATTCCC-3' (SEQ ID NO: 11)). The *vibrio cholerae* N16961 strain (AE003852) was used as a template for CTA1. The PCR amplified CTA1 product was digested with Xho I (Cat. No. R0146S, New England Biolabs, Beverly, Mass.) and BamH I (Cat. No. R0136S, NEB) and ligated to the pET15b-Tat-GFP-Tat plasmid which was linearized with same enzymes resulting in the recombinant plasmid pET15b-TCTA1T. Plasmid, pET15b-TmCTA1T, which expressing mutant CTA1 at ADP ribosyltransferase enzymetic active site (Ser-63→Lys) was generated by site-directed mutagenesis with 5'-TATGTTTCCACCAAGATTAGTTTGAGA-3' (SEQ ID NO: 12) and 5'-TCTCAAACTAATCTTGGTGGA AACATA-3 (SEQ ID NO: 13) primers by Pyrobest DNA polymerase (Cat. No. R005, Takara, Japan). pET15b-TCTA1T plasmid was used as a template for TmCTA1T. Dpn I (Cat. No. R0176S, NEB) was added directly to the PCR products and then was transformed into DH5a competent cells (Cat. No. YE608, Yeastern Biotech Co., Taiwan). Next day each single colony was cultured into 1.5 ml of LB broth. Each plasmid was purified with QIAprep spin miniprep kit (Cat. No. 27106, QIAgen, Valencia, Calif.). The sequence of pET15b-TmCTA1T was confirmed at Macrogen (Seoul, Korea). For CTA1, the gene was amplified by PCR using a forward primer (5'-CCCGGG CATATGAATGATGATAAGTTATATCGG-3' (SEQ ID NO: 14)) and a reverse primer (5'-CCCGGG GGATCCCTACGATGATCTTGGAGCATT-3' (SEQ ID NO 15)) The pET15b-TCTA1T plasmid was used as a template for CTA™. The PCR product and pET15b vector were digested with Nde I (Cat. No. R0111S, New England Biolabs, Beverly, Mass.) and BamH I (Cat. No. R0136S, NEB). The PCR product was ligated into pET15b vector by T4 DNA ligase (Cat. No. M0202S, NEB). The pET15b-CTA1 plasmid was sequenced at Macrogen (Seoul, Korea). The sequences of these constructs and relevant amino acid fragments are shown in FIGS. 14A-D and FIGS. 15A-C.

Expression and Purification of TCTA1T and TmCTA1T Proteins in *E. Coli*

Recombinant proteins were expressed in *E. coli* BL21 (DE3) strain (Cat. No. 69387, Novagen, Germany) transformed with the pET15b-TCAT1T, pET15b-CAT1 or pET15b-TmCTA1T. The cells were grown in 1 liter of LB medium containing 100 μg/ml of ampicillin at 37° C. until $OD_{600}$ reached 0.6. Isopropyl-β-D-thiogalactopyranoside (IPTG) was then added to a final concentration of 0.5 mM. Cells were incubated for additional 4 h at 37° C. and finally harvested by centrifugation at 6000 rpm for 10 min. The cell pellet was suspended in a binding buffer (20 mM Tris-Cl, 0.5 M NaCl, 10% glycerol, pH 8.0) and the cells were lysed by sonication. The soluble and insoluble fractions were separated by centrifugation for 30 min at 18,000 rpm. The insoluble fraction was dissolved in binding buffer containing 6 M urea. After centrifugation for 30 min at 18,000 rpm, the supernatant was applied to a Talon metal affinity column (Clontech, Palo Alto, Calif.). The column was washed with wash buffer (20 mM Tris-Cl, 0.5 M NaCl, 30 mM imidazole, 10% glycerol, pH 8.0) and protein was eluted with elution buffer (20 mM Tris-Cl, 0.5 M NaCl, 0.3 M imidazol, 10% glycerol, pH 7.9). The purified proteins were stored at −80° C.

Immunization of Mice

Six-week-old female BALB/c mice (Orient, Korea) were immunized intranasally (i.n.) with OVA (20 or 200 μg as indicated; Cat. No. A5503, Sigma, St. Louis, Mo.) alone or mixed with 10 μg of CTA1, TCTA1T, TmCTA1T or 2 μg of CT (Cat. No. 101A; List Biological Laboratories Inc., Campbell, Calif.) in 20 μl of PBS on day 0, 14, and 28 (n=5 per group). To determine the optimal dose of adjuvant, another set of mice were immunized three times at two-week intervals intra-nasally (i.e., "i.n.") with 20 μg of OVA alone or mixed with 0.1, 1.0, 10, or 20 μg of TCTA1T. In a separate set of experiments, BALB/c mice were immunized two times at 14 day intervals i.n with 10 μg of recombinant influenza M2 protein and 10 μg of TCTA1T as an adjuvant. At 2 weeks after immunization, the mice were challenged with 10 $LD_{50}$ of A/PR/8 virus i.n. and monitored for body weight and survival.

Collection of Samples

Mice were anesthetized by intraperitoneal (i.e., "i.p.") injection of ketamine (Yuhan Co., Korea). Blood was collected from the retro-orbital plexus 12 days after each immunization and serum was obtained from blood by centrifugation for 10 min at 13,000 rpm. Saliva samples were obtained after inducing salivary gland secretion by i.p. injection of pilocarpine (100 μl of 1 mg/ml; Cat. No. P6503, Sigma, St. Louis, Mo.) 2 weeks after each immunization. Nasal and lung lavages were collected on day 42. Anesthetized mice were dissected to expose the trachea and IV catheter (Cat. No. 591836, BD Biosciences, San Jose, Calif.) was inserted into a small nick of the trachea. Lung washes were performed by repeated flushing and aspiration with 500 μl of PBS into the lungs. Nasal washes were collected by flushing with 50 μl of PBS two times through the nasal cavity. Lung tissues were cut in small pieces and subjected to do freeze-thaw cycles two times. Tissues were centrifuged at 13,000 rpm at 4° C. for 10 min and supernatant was collected to test for Ag-specific Ab responses.

Measurement of Antigen-Specific Antibodies

OVA-specific antibody response was determined by enzyme-linked immunosorbent assay (ELISA). To measure the antibody responses, OVA protein was diluted to 1 mg/ml with 50 mM sodium bicarbonate buffer (pH 9.6). ELISA plates (Cat. No. 439454, Nunc, Denmark) were coated with 100 μl of the diluted protein per well and incubated at 4° C. overnight. Plates were washed with PBS and blocked with 5% skin milk in PBS for 1 h at room temperature. Serum or mucosal samples were diluted in the blocking buffer at two-fold dilution series. Diluted samples were added into the wells and incubated for 1 h at 37° C. After a wash with PBS, each well was treated with 100 μl of Goat-anti-mouse IgG-horseradish peroxidase (HRP; Cat. No. sc-2005 Santa cruz Biotechnology, Santa Cruz, Calif.) conjugates or Goat-anti-mouse IgA-HRP (Cat. No. sc-3791, Santa Cruz, Calif.) diluted with the blocking buffer, and the plates were incubated for 1 h at room temperature. Color was developed with 100 μl of the substrate TMB (3,3',5,5'-tetramethylbenzidine) solution (ES001, Millipore, Billerica, Mass.) for 20 min in the dark. The reaction was stopped by the addition of 50 μl. 1 of 0.5 N HCl. The absorbance measured at 450 nm by a microplate reader (Molecular Devices Corp., Menlo Park, Calif.). For each group of immunization, results were expressed as geometric mean titer (GMT)+S.D.

ELISPOT Assays

Spleen and lung single-cell suspensions were prepared on day 7 after final immunization and assayed for frequencies of specific antibody-secreting cells (ASC) by the ELISPOT assay as previously described [29]. Nitrocellulose microplates (Cat. No. MAHAN4510, Millipore) were coated with OVA (1 mg/ml) and incubated at 4° C. overnight. Plates were washed and wells were blocked with RPMI medium containing 10% FBS (Cat. No. 14-501F, Biowhittaker, Walkersville, Md.) for 30 min at room temperature. Serially diluted cells in blocking buffer were added to the plates and incubated for 3 hrs at 37° C. After 4 washings with PBS, HRP-conjugated goat anti-mouse IgG (Cat. No. 1030-05, Southern Biotechnology Associates, Birmingham, Ala.) or IgA Abs (Cat. No. 1040-05, Southern Biotechnology Associates) were then added to the plates for 1 hr at ambient temperature. After another round of washes with PBS, plates were incubated with AEC-H2O2 chromogenic substrate (Cat. No. A5754, Sigma-Aldrich) and spots indicating the former location of specific ASCs were counted under a stereomicroscope. Results were expressed as the mean spot-forming cells (SFC)/$10^6$ cells.

In Vivo CTL Assay

In vivo CTL assay was performed as previously described [30] with minor modifications. Spleen cells from C57BL/6 mice were split into two fractions. One fraction was labeled with 5 μM carboxyfluorescein succinimidyl ester (CFSE) (Cat. No. V12883, Invitrogen, Carlsbad, Calif.) for 5 min at room temperature and pulsed with 1 μM OVA SIINFEKL peptide (SEQ ID NO: 16), a synthetic peptide containing the amino acid sequence a.a. 257-264 of ovalbumin (OVA), for 1 h at 37° C. The other fraction was labeled with 0.5 μM CFSE without peptide pulse. Both fractions were mixed and injected intravenously into recipient C57BL/6 mice that had been previously immunized with OVA and the indicated adjuvant. Single cell suspensions were then prepared from lung and spleen from recipient mice, 24 h after cell transfer. Specific killing activity was measured by flow cytometry.

Toxicity Test

To assess footpad edema [31], anesthetized mice with ketamine were injected with 20 μg of TCTA1T, CTA1, TmCTA1T or 1 μg of CT in 10 μl of PBS into the hind paw. The thickness of the footpad was measured after 24 h.

To perform the intestinal loop test [32], mice were anesthetized with ketamine and the abdomen was opened to make a 3 to 5 cm loop in the middle part of the small intestine. Two micrograms of CT, 20 μg of TCTA1T, 20 μg of CTA1, or 20 μg of TmCTA1T in 100 μl of PBS were injected into the loops. The abdomen was closed and the loops with its fluid content were weighed and its length was determined after 6 h.

BHK21 cells (ATCC No. CCL-10) were seeded at 1×$10^6$ cells/well in 6 well plate. One day later, cells were washed with serum-free medium and incubated with 1 μg of CT, 10 μg of TCTA1T, CTA1, or TmCTA1T for 3 h. Supernatants were obtained by centrifugation at 1,000×g, for 10 min. The concentration of cAMP in the supernatant was measured by cyclic AMP EIA kit (Cat. No. 581001, Cayman) according to the manufacturer's instructions.

In order that this invention may be better understood, the following examples are set forth. The examples are for the purpose of illustration only and are not to be construed as limiting the scope of the invention.

EXAMPLES

Example 1

Construction and Characterization of Recombinant PTD-CTA1

TCTA1T was constructed by attaching PTD from HIV Tat at both N- and C-terminus of CTA1 in frame. Duel attachment of PTD enhances cellular uptake more than that of single PTD attachment. A mutant CTA1 containing an ADP ribosyltransferase enzymatically active site, (TmCTA1T), was generated and purified using the same process as used for TCTA1T, for use as a negative control. All the constructs were confirmed by DNA sequencing analysis. The proteins purified by metal affinity chromatography were analyzed by SDS-PAGE and showed a single distinct band of 27 kDa, which corresponded well to the expected size of TCTA1T and TmCTA1T (FIG. 1) Western blot analysis by using CTA1-specific monoclonal antibodies confirmed the expression of CTA1.

Example 2

TCTA1T Enhances Systemic and Mucosal Antibody Responses

To test the adjuvant activity of TCTA1T, groups of mice were immunized three times i.n. with 20 μg of OVA co-mixed with TCTA1T (10 μg), TmCTA1T (10 μg) or CT (2 μm) and sera were collected on days 0, 14, 28 and 42 to analyze OVA-specific IgG responses by ELISA.

As shown in FIG. 2, immunization with TCTA1T enhanced the total serum Ig anti-OVA which is comparable to that of CT adjuvant. The ADP-ribosylation inactive mutant, TmCTA1T, enhanced total IgG responses substantially higher than that of control group which immunized only with OVA but the level of antibodies was much lower than that of TCTA1T and CT indicating the importance of active ADP ribosyltransferase for the optimal adjuvant activity.

These IgG responses were predominantly IgG1 isotype and IgG2a anti-OVA antibody responses were significantly increased after third immunization in the group of mice immunized together with TCTA1T or CT (FIG. 2).

Anti-OVA IgA antibody titers in saliva, nasal washes and lung tissue were analyzed after third immunization to asses the adjuvant activities for mucosal immune responses (FIG. 3).

Intranasal immunization with OVA plus TCTA1T generated high anti-OVA IgA antibody responses in all of these mucosal samples, and these responses were of the same magnitude as those induced by immunization with OVA plus CT (FIG. 3). However, mucosal OVA-specific antibody responses were not detectable after immunization with OVA alone or were very low in the mice immunized with OVA plus TmCTA1T (FIG. 3).

Figure 4A:
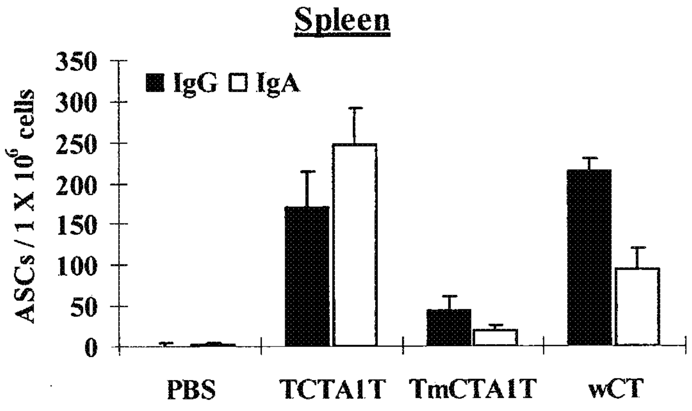
FIGS. 4A-B show OVA-specific Ab producing cells in spleen (FIG. 4A) and lung (FIG. 4B) of mice immunized nasally with TCTA1T, TmCTA1T or CT. Ab producing cells were measured on day 7 after third immunization.
Figure 4B:
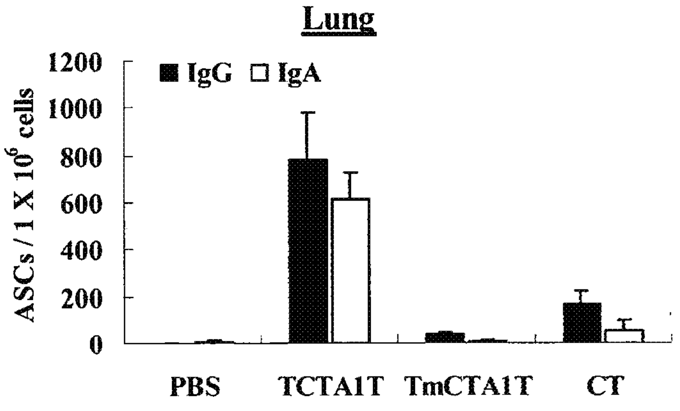

Large numbers of OVA-specific antibody-secreting cells (ASC) were detected in the spleen (FIG. 4A) and lung cell suspensions after third immunization with OVA plus TCTA1T (FIG. 4B). The number of IgA class OVA specific ASCs from the spleen of mice immunized with OVA plus TCTA1T was higher than that of mice immunized with OVA plus CT (FIG. 4A). More interestingly, TCTA1T generated roughly 5-(IgG class) or 10-times (IgA class) higher ASCs in the lung than that of CT (FIG. 4B). The TmCTA1T, which was expressed and purified as like TCTA1T, failed to increase the number of ASCs significantly.

Figure 5A:
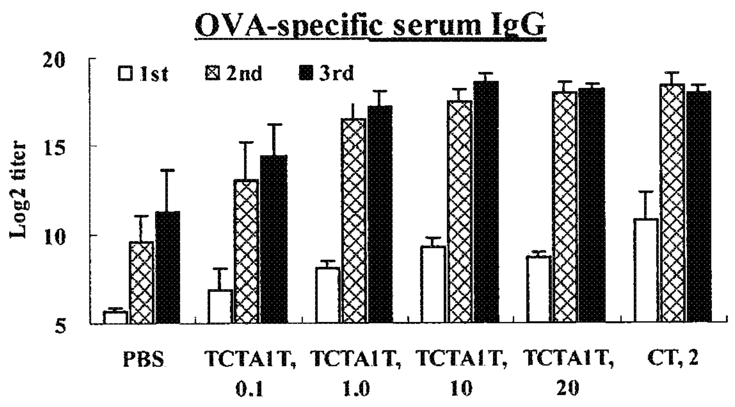
FIGS. 5A-B show OVA-specific mucosal and systemic antibody responses of mice immunized nasally with various doses of TCTA1T as an adjuvant. Saliva and Serum were collected on days 13, 27, 41.
Figure 5B:
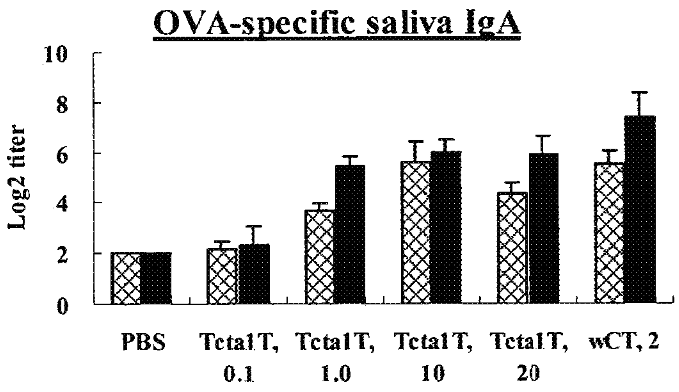

A dose response analysis was performed with TCTA1T in comparison with 2 μg of CT to find out optimal dose of immunization as a systemic and mucosal adjuvant (FIG. 5A-B). TCTA1T augmented OVA-specific serum IgG responses at a dose of 0.1 μg and IgA responses at a dose of 1 μg (FIGS. 5A and 5B). The OVA-specific antibody responses showed a linear dose response activity until 10 μg of TCTA1T which gave comparable enhancement of OVA-specific IgG and IgA antibody responses to that 2 μg of CT.

Taken together, these data showed that TCTA1T exhibited strong mucosal adjuvant activities for enhancing systemic IgG and mucosal IgA immune responses which were comparable to that stimulated by CT.

Example 3

TCTA1T Enhances In Vivo CTL Responses

The co-delivery of CT with soluble protein antigen is well known to enhance antigen-specific cytotoxic T cell responses [33]. To assess the CTL activity of TCTA1T, in vivo cytolytic assays were performed in the spleen and lung against the OVA257-264 epitope (SIINFEKL peptide (SEQ ID NO: 16)) which is recognized by H-2 Kb MHC class 1 molecules (FIG. 6). Groups of mice were given three spaced immunizations, 14 days apart, with 200 μg of OVA and TCTA1T, TmCTA1T or CT.

The in vivo CTL activity elicited by the TCTA1T is slightly lower than that by the CT but still much higher than those by the TmCTA1T and OVA alone in both lung and spleen (FIG. 6). These data indicate that TCTA1T is a strong adjuvant for inducing systemic and mucosal CD8+ cytotoxic T cell responses.

Example 4

TCTA1T Enhances Protective Immunity in Mice

M2 protein of influenza A virus is well conserved in all human influenza A strains and has been used to develop universal flu vaccine. Recently, it was reported that mucosal vaccination of M2 with CT is superior to parenteral vaccination for the protection against lethal virus challenge. In view of this advantage of mucosal vaccination, we explored the possibility of TCTA1T as a potent mucosal adjuvant for M2-based vaccine.

Figure 7A:
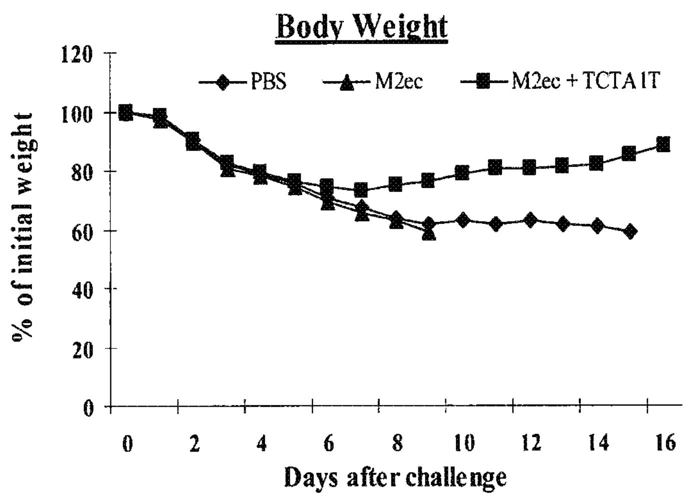
FIG. 7A-B show weight loss (FIG. 7A) and survival (FIG. 7B) in mice challenged by intranasal inoculation with 10 $LD_{50}$ of A/PR/8, 2 weeks after the second immunization.
Figure 7B:
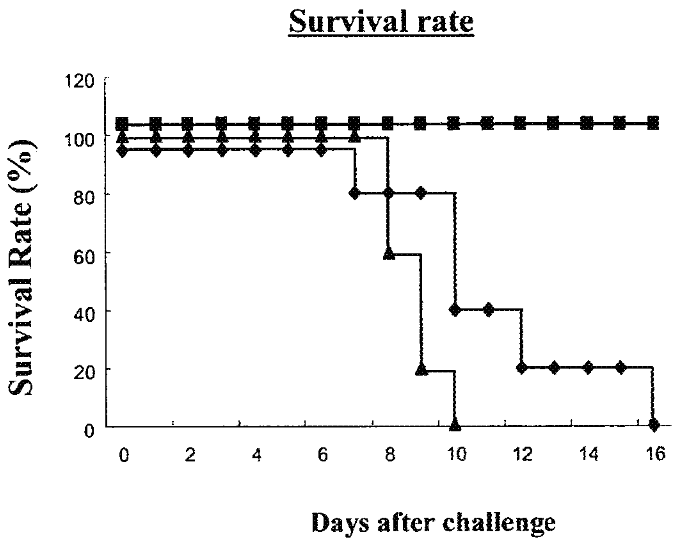

Co-administration of recombinant influenza M2 protein with TCTA1T resulted in complete protection against lethal influenza virus challenge (FIG. 7B). None of the mice immunized i.n. with M2 alone or PBS were survived after challenge with 10 $LD_{50}$ of $H1N_1$ influenza virus and displayed more significant weight loss when compared to the TCTA1T adjuvanted group (FIG. 7A-B).

Example 5

TCTA1T is Safe as a Mucosal Adjuvant

CT is very strong mucosal adjuvant, but high toxicity prevents it to use as an adjuvant for humans. TCTA1T enter the cells very efficiently following non-specific binding through PTD which is different from CT that uses ganglioside $G_{M1}$ receptor for receptor mediated endocytosis. Therefore, CTA1 part from TCTA1T might be localized at different subcellular site from CTA1 of CT. To asses the toxicity of TCTA1T, three classical CT toxicity test with minor modifications were performed: the cAMP secretion test in BHK21 cells, the footpad edema test, and the loop ligation test in mice (FIG. 8). TCTA1T induced the secretion of cAMP but the level of cAMP was much lower than that of CT. CT showed strong toxicities in the footpad edema and the loop ligation test, TCTA1T, however, did not exhibit any toxic symptoms (FIG. 8).

Example 6

Construction and Expression of CTA1

Figure 9A:
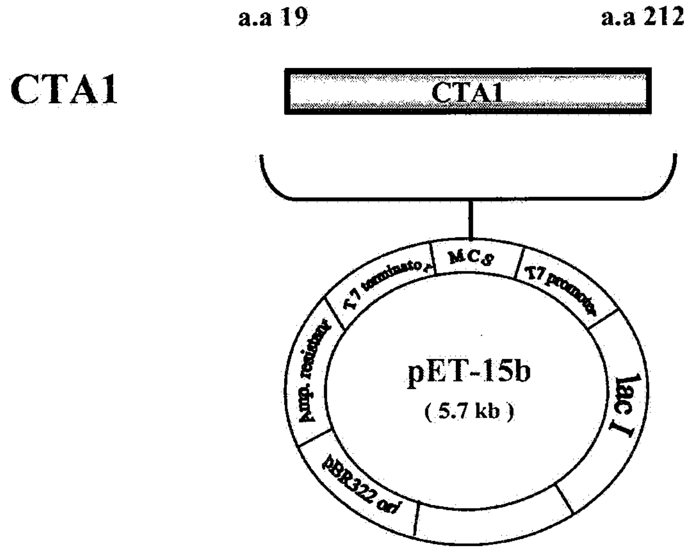
FIGS. 9A-B show a schematic representation of CTA1 expression vector (FIG. 9A) and purification of the CTA1 protein from *E. coli* (FIG. 9B).
Figure 9B:
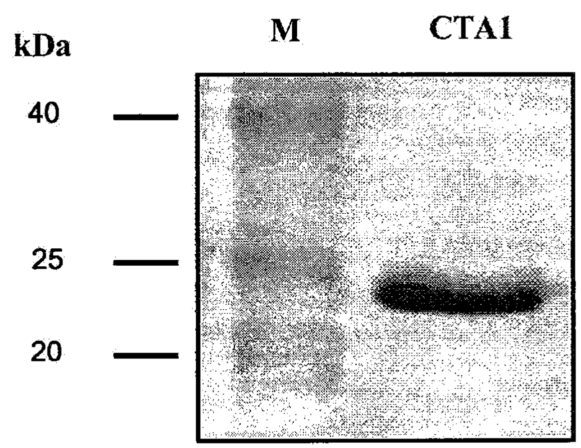

The CTA1 expression vector, pET15b-TCAT1T (FIG. 9A), was confirmed by sequence analysis and then the protein was purified by metal affinity chromatography which showed a single distinct band of 24 kDa at the SDS-PAGE analysis (FIG. 9B).

Example 7

CTA1 Enhances Systemic and Mucosal Antibody Responses

As shown in FIG. 10A, immunization with CTA1 enhanced the total serum IgG anti-OVA which is comparable to that of CT adjuvant. Anti-OVA IgA antibody titers in saliva and lung tissue were analyzed after third immunization to assess the adjuvant activities for mucosal immune responses (FIG. 10B-C).

Intranasal immunization with OVA plus CTA1 generated high anti-OVA IgA antibody responses in saliva and lung samples with similar magnitude as those induced by immunization with OVA plus CT (FIG. 10B-C).

Figure 11A:
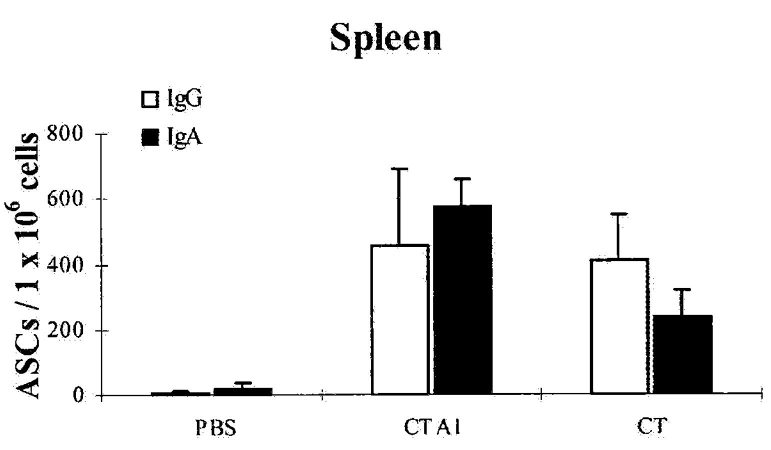
FIG. 11A-B show OVA-specific Ab producing cells in spleen (FIG. 11A) and lung (FIG. 11B) of mice immunized nasally with CTA1 plus OVA. Ab producing cells were measured on day 7 after the third immunization.
Figure 11B:
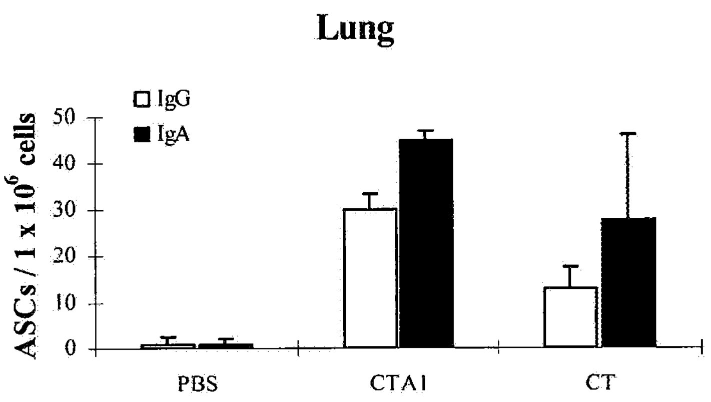

Large numbers of OVA-specific antibody-secreting cells (ASC) were detected in the spleen (FIG. 11A) and lung cell suspensions (FIG. 11B) after third immunization with OVA plus CTA1.

Example 8

CTA1 Enhances In Vivo CTL Responses

OCA-specific CD8+ cytotoxic T cell response was determined in spleen and lung of mice immunized nasally with CTA1 plus OVA. The co-administration of CTA1 with OVA generated high level of OVA-specific in vivo CTL activity in both lung and spleen (FIG. 12). These data indicate that CTA1 also could be a strong adjuvant for inducing systemic and mucosal CD8+ cytotoxic T cell responses.

Example 9

CTA1 is a Non-Toxic Adjuvant

Because the CTA1 fragment lacks the CTB moiety, it cannot enter the cell through ganglioside $G_{M1}$/receptor mediated endocytosis. However, it still has active ADP ribosyltransferase and consequently, has the potential to exhibit toxic effects.

To test for any toxic effects relating to the ADP ribosyltransferase activity of CTA1, footpad edema and the loop ligation tests were performed in mice. As shown in FIG. 13A, CTA1 induced the secretion of cAMP but the level of cAMP was much lower than that of CT. CTA1 did not exhibit any toxic symptoms in the footpad edema (FIG. 13B) or in the loop ligation test in mice (FIG. 13C).

Constructs of the present invention illustrate that contrary to various previous studies, CTA1, which exhibits the ADP ribosyl transferase activity of CTA, is non-toxic and displays strong adjuvant properties. Additionally, a mutated form of CTA1 lacking ADP ribosylating activity also lacks adjuvant properties. These findings are unexpected and indicate that the ADP ribosylating activity of CTA1 (and also CTA and of the native CT) is necessary for adjuvanticity but dispensable for toxicity.

The present invention is based in part on the unexpected finding that CTA1 can display adjuvant properties without requiring conjugation to a cell surface receptor binding moiety. Further, the present invention shows that conjugation of CTA1 to a polypeptide belonging to the class of polypeptides containing a protein transduction domain, also called PTD or cell-penetrating peptides, and known to penetrate across mammalian cell membranes irrespective of cell type, can be utilized to enhance the adjuvant properties of CTA1, presumably by facilitating the passage of CTA1 across cell membranes in a cell surface receptor-independent manner.

Example 10

CTA1 does not Induce Antibodies to Itself

Six- to eight-week old female BALB/c mice (Orient, Korea) were anesthesized by intraperitoneal injection of ketamine (Yuhan Corporation, Seoul, Korea). TCTA1T and cholera toxic (CT) (List Biological Laboratories) were diluted in PBS. The mice were given 10 ug of TCTA1T or 2 ug of CT administered intranasally (i.n.) or sublingually (s.l.) on 3 consecutive occasions at 14-day intervals. For the s.l. route, mice were administered with 15 ul of proteins by a thin pipette applied against the ventral side of the tongue and directed toward the floor of the mouth. Animals were maintained with heads placed in ante flexion for 30 min. For the i.n. route, proteins were administered in a total volume of 15 ul and split into each nostril. Blood was collected from the retro-orbital plexus on day 12-14 after each administration and sera were obtained from blood by centrifugation at 13,000 rpm for 10 min. (A) TCTA1T-specific and (B) CT-specific IgG Ab responses in sear were determined by ELISA. To measure the antibody responses, TCTA1T and CT proteins were diluted to 3 ug/ml and 1 ug/ml, respectively, in 50 mM sodium bicarbonate buffer, pH 9.6. Microtiter plates (Nunc, Denmark) were coated with 100 ul of the diluted protein per well and incubated at 4° C. overnight. Plates were washed with PBS and blocked with 5% skim milk in PBS (blocking buffer) for 1 h at room temperature. Serial five-fold dilutions of serum samples were prepared in blocking buffer, added under 100 ul volumes into the wells, and incubated for 1 h at 37° C. After a wash with PBS, each well was incubated with 100 ul of goat-anti-mouse IgG-horseradish peroxidase (HRP) conjugate (Southern Biotechnology Associates, Birmingham, Ala., USA) diluted to 1/1000 with blocking buffer, and the plates were further incubated for 1 h at room temperature. Following wash with PBS, enzyme-bound activity was monitored after addition of 100 ul/well of chromogenic substrate consisting of TMB (3,3',5,5'-tetramethylbenzidine) (Sigma) and 0.05% H2O2 solution for 20 min in dark. The reaction was stopped by addition of 50 ul of 0.5 N HCl (Sigma). The absorbance of individual wells was measured at 450 nm with a microplate reader (Molecular Devices Corp., Menlo Park, Calif.). The results are expressed as geometric mean antibody titer (GMT)±S.E.M. for each experimental group of animals. The titer of a given serum sample was defined as the reciprocal of the highest dilution of said sample giving as absorbance value over thrice that a of a pool of control sera. The results depicted in FIGS. 16A and B show that TCTAIT does not induce antibodies to itself 1. Holmgren, J. and C. Czerkinsky, *Mucosal immunity and vaccines*. Nat Med, 2005. 11(4 Suppl): p. S45-53.
2. Kiyono, H., et al., *The mucosal immune system: features of inductive and effector sites to consider in mucosal immunization and vaccine development*. Reg Immunol, 1992. 4(2): p. 54-62.
3. McGhee, J. R., et al., *The mucosal immune system: from fundamental concepts to vaccine development*. Vaccine, 1992. 10(2): p. 75-88.
4. De Haan, L. and T. R. Hirst, *Cholera toxin: a paradigm for multi functional engagement of cellular mechanisms (Review)*. Mol Membr Biol, 2004. 21(2): p. 77-92.
5. Czerkinsky, C., et al., *Mucosal immunity and tolerance: relevance to vaccine development*. Immunol Rev, 1999. 170: p. 197-222.
6. Wu, H. Y. and H. L. Weiner, *Oral tolerance*. Immunol Res, 2003. 28(3): p. 265-84.
7. Agren, L. C., et al., *Genetically engineered nontoxic vaccine adjuvant that combines B cell targeting with immunomodulation by cholera toxin A*1 *subunit*. J Immunol, 1997. 158(8): p. 3936-46.
8. Hornquist, E. and N. Lycke, *Cholera toxin adjuvant greatly promotes antigen priming of T cells*. Eur J Immunol, 1993. 23(9): p. 2136-43.
9. Freytag, L. C. and J. D. Clements, *Mucosal adjuvants*. Vaccine, 2005. 23(15): p. 1804-13.
10. O'Neal, C. M., et al., *Rotavirus* 2/6 *virus like particles administered intranasally with cholera toxin, Escherichia coli heat-labile toxin* (*LT*), *and LT-R*192*G induce protection from rotavirus challenge. J Virol*, 1998. 72(4): p. 3390-3.
11. Hagiwara, Y., et al., *Mutants of cholera toxin as an effective and safe adjuvant for nasal influenza vaccine*. Vaccine, 1999. 17(22): p. 2918-26.
12. Porgador, A., et al., *Intranasal immunization with cytotoxic T-lymphocyte epitope peptide and mucosal adjuvant cholera toxin: selective augmentation of peptide presenting dendritic cells in nasal mucosa-associated lymphoid tissue*. Infect Immun, 1998. 66(12): p. 5876-81.
13. Ruiz-Bustos, E., et al., *Protection of BALB/c mice against experimental Helicobacter pylori infection by oral immunisation with H pylori heparan sulphate-binding proteins coupled to cholera toxin beta-subunit*. J Med Microbiol, 2000. 49(6): p. 535-41.
14. Gagliardi, M. C., et al., *Cholera toxin induces maturation of human dendritic cells and licences them for Th*2 *priming*. Eur J Immunol, 2000. 30(8): p. 2394-403.
15. Ohmura, M., et al., *Highly purified mutant E*112*K of cholera toxin elicits protective lung mucosal immunity to diphtheria toxin*. Vaccine, 2001. 20(5-6): p. 756-62.
16. Yamamoto, S., et al., *Mutants in the ADP-ribosyltransferase cleft of cholera toxin lack diarrheagenicity but retain adjuvanticity*. J Exp Med, 1997. 185(7): p. 1203-10.
17. Yamamoto, S., et al., *A nontoxic mutant of cholera toxin elicits Th*2*-type responses for enhanced mucosal immunity*. Proc Natl Acad Sci USA, 1997. 94(10): p. 5267-72.
18. Yamamoto, M., et al., *Genetically manipulated bacterial toxin as a new generation mucosal adjuvant*. Scand J Immunol, 2001. 53(3): p. 211-7.
19. Agren, L. C., et al., *Adjuvanticity of the cholera toxin A*1*-based gene fusion protein, CTA*1*-DD, is critically dependent on the ADP-ribosyltransferase and Ig-binding activity*. J Immunol, 1999. 162(4): p. 2432-40.
20. Aa Lena C., et al., *Adjuvanticity of Cholera Toxin A*1-based gene fusion protein, CTA1-*DD, is critically dependent on the ADP-Ribosyltransferase and Ig-Binding Activity*1. The Journal of Immunology, 1999, 162: p. 2432-2440.
21. Campos, E. A., et al., *Nasally administered cholera toxin A-subunit acts as a mucosal adjuvant*. J Oral Sci, 2003. 45(1): p. 25-31.

20A. Kabouridis P S. *Biological applications of protein transduction technology*. TRENDS in Biotechnology, 2003, 21(11): p 498-503.

22. Derossi, D., et al., *The third helix of the Antennapedia homeodomain translocates through biological membranes*. J Biol Chem, 1994. 269(14): p. 10444-50.
23. Schwarze, S. R. and S. F. Dowdy, *In vivo protein transduction: intracellular delivery of biologically active proteins, compounds and DNA*. Trends Pharmacol Sci, 2000. 21(2): p. 45-8.
24. Lewin, M., et al., *Tat peptide-derivatized magnetic nanoparticles allow in vivo tracking and recovery of progenitor cells*. Nat Biotechnol, 2000. 18(4): p. 410-4.
25. Torchilin, V. P., TAT *peptide-modified liposomes for intracellular delivery of drugs and DNA*. Cell Mol Biol Lett, 2002. 7(2): p. 265-7.
26. Torchilin, V. P., et al., *TAT peptide on the surface of liposomes affords their efficient intracellular delivery even at low temperature and in the presence of metabolic inhibitors*. Proc Natl Acad Sci USA, 2001. 98(15): p. 8786-91.

27. Tseng, Y. L., J. J. Liu, and R. L. Hong, *Translocation of liposomes into cancer cells by cell-penetrating peptides penetration and tat: a kinetic and efficacy study*. Mol Pharmacol, 2002. 62(4): p. 864-72.

28. Ryu, J., et al., *Enhanced uptake of a heterologous protein with an HIV-1 Tat protein transduction domains (PTD) at both termini*. Mol Cells, 2003. 16(3): p. 385-91.

29. Teter, K., et al., *The cholera toxin A1 (3)subdomain is essential for interaction with ADP-ribosylation factor 6 and full toxic activity but is not required for translocation from the endoplasmic reticulum to the cytosol*. Infect Immun, 2006. 74(4): p. 2259-67.

30. Johansson, E. L., et al., *Antibodies and antibody-secreting cells in the female genital tract after vaginal or intranasal immunization with cholera toxin B subunit or conjugates*. Infect Immun, 1998. 66(2): p. 514-20.

31. Coles, R. M., et al., *Progression of armed CTL from draining lymph node to spleen shortly after localized infection with herpes simplex virus 1*. J Immunol, 2002. 168(2): p. 834-8.

32. Lexomboon, U., et al., *Clinical evaluation of co-trimoxazole and furazolidone in treatment of shigellosis in children*. Br Med J, 1972. 3(5817): p. 23-6.

33. Lange, S. and J. Holmgren, *Protective antitoxic cholera immunity in mice: influence of route and number of immunizations and mode of action of protective antibodies*. Acta Pathol Microbiol Scand [C], 1978. 86C(4): p. 145-52.

34. Bowen, J. C., et al., *Cholera toxin acts as a potent adjuvant for the induction of cytotoxic T-lymphocyte responses with non-replicating antigens*. Immunology, 1994. 81(3): p. 338-42.

35. U.S. Pat. No. 5,917,026

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. It is further to be understood that all values are approximate, and are provided for description.

Patents, patent applications, publications, product descriptions, and protocols are cited throughout this application, the disclosures of which are incorporated herein by reference in their entireties for all purposes.

What is claimed is:

1. A fusion protein comprising an A1 subunit of a bacterial enterotoxin selected from the group consisting of cholera toxin A1 and *Escherichia coli* heat-labile enterotoxin A1, conjugated at the amino terminus, carboxy terminus, or both amino and carboxy terminus with a polypeptide belonging to the class of protein transduction domains or cell-penetrating peptides.

2. The fusion protein of claim 1, wherein the fusion protein is capable of augmenting an immune response to a co-administered antigen.

3. The fusion protein of claim 1, wherein the fusion protein does not induce antibodies to said A1 subunit.

4. The fusion protein of claim 1, wherein the enterotoxin comprises a subunit with ADP ribosyl transferase activity.

5. The fusion protein of claim 4, wherein the subunit is the ADP-ribosylating A1 subunit of cholera toxin.

6. The fusion protein of claim 1, wherein the enterotoxin comprises an ADP-ribosylating A1 subunit of *Escherichia coli* heat-labile enterotoxin.

7. The fusion protein of claim 1, wherein the protein transduction domain or cell-penetrating peptide is the HIV-1 Tat protein transduction domain.

8. The fusion protein of claim 1, which comprises an amino acid sequence of SEQ ID NO:5.

9. A vaccine composition comprising a) the fusion protein of claim 1, b) an antigen, and c) a pharmaceutically acceptable carrier or diluent, wherein the amounts of a) and b) in combination are effective to elicit an immune response to said antigen.

10. The vaccine composition of claim 9, wherein said vaccine is administered by a mucosal or a systemic route.

11. The vaccine composition of claim 10, capable of inducing a mucosal immune response.

12. The vaccine composition of claim 11, wherein the mucosal immune response is a secretory antibody response.

13. The vaccine composition of claim 11, wherein said mucosal immune response is a mucosal cytotoxic T lymphocyte response.

14. The vaccine composition of claim 10 capable of inducing a systemic immune response.

15. The vaccine composition of claim 14, wherein the systemic immune response is a serum antibody response.

16. The vaccine composition of claim 14, wherein the systemic immune response is a systemic cytotoxic T lymphocyte response.

17. An immunogenic composition comprising a) the fusion protein of claim 1, b) an antigen, and optionally c) a pharmaceutically acceptable carrier or diluent, wherein the amounts of a) and b) in combination are effective to elicit an immune response.

18. A kit comprising the vaccine composition according to claim 9.

19. A kit comprising the fusion protein according to claim 1.

20. The vaccine composition of claim 9, comprising from about 1 μg to about 1 mg of the fusion protein of claim 1.

* * * * *